United States Patent
Zdanowski et al.

(10) Patent No.: US 11,813,376 B2
(45) Date of Patent: *Nov. 14, 2023

(54) CELLULAR COMPOSITIONS DERIVED FROM DECEASED DONORS TO PROMOTE GRAFT TOLERANCE AND MANUFACTURE AND USES THEREOF

(71) Applicant: MEDEOR THERAPEUTICS, INC., South San Francisco, CA (US)

(72) Inventors: Michael Zdanowski, Fort Salonga, NY (US); Colby Suire, Houston, TX (US); D. Scott Batty, Jr., San Carlos, CA (US)

(73) Assignee: MEDEOR THERAPEUTICS, INC., South San Francisco, CA (US)

(*) Notice: Subject to any disclaimer, the term of this patent is extended or adjusted under 35 U.S.C. 154(b) by 1047 days.

This patent is subject to a terminal disclaimer.

(21) Appl. No.: 16/574,867

(22) Filed: Sep. 18, 2019

(65) Prior Publication Data
US 2020/0086006 A1   Mar. 19, 2020

Related U.S. Application Data

(60) Provisional application No. 62/732,823, filed on Sep. 18, 2018.

(51) Int. Cl.
*A61K 35/12* (2015.01)
*A61L 27/38* (2006.01)
*C07K 14/725* (2006.01)
*C07K 14/74* (2006.01)

(52) U.S. Cl.
CPC .......... *A61L 27/3834* (2013.01); *A61K 35/12* (2013.01); *C07K 14/7051* (2013.01); *C07K 14/70539* (2013.01); *A61K 2035/122* (2013.01); *A61L 2430/40* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,607,579 A | 3/1997 | Latham, Jr. et al. |
| 5,876,708 A | 3/1999 | Sachs |
| 6,280,957 B1 | 8/2001 | Sayegh et al. |
| 6,544,506 B2 | 4/2003 | Reisner |
| 6,558,662 B2 | 5/2003 | Sykes et al. |
| 6,743,192 B1 | 6/2004 | Sakota et al. |
| 6,877,514 B2 | 4/2005 | Sykes |
| 7,270,810 B2 | 9/2007 | Reisner et al. |
| 7,288,255 B1 | 10/2007 | Shlomchik et al. |
| 7,297,329 B2 | 11/2007 | Akashi et al. |
| 7,332,157 B2 | 2/2008 | Sykes |
| 7,638,121 B2 | 12/2009 | Sykes |
| 7,776,591 B2 | 8/2010 | Xia et al. |
| 7,811,815 B2 | 10/2010 | Brown |
| 7,939,062 B2 | 5/2011 | Sykes |
| 8,734,786 B2 | 5/2014 | Miller et al. |
| 8,916,147 B2 | 12/2014 | Reisner |
| 8,980,329 B2 | 3/2015 | Brown |
| 9,090,871 B2 | 7/2015 | Durrant et al. |
| 9,364,600 B2 | 6/2016 | Pages et al. |
| 9,452,184 B2 | 9/2016 | Ildstad et al. |
| 9,504,717 B2 | 11/2016 | Strober et al. |
| 9,545,427 B2 | 1/2017 | Brown |
| 9,561,253 B2 | 2/2017 | Strober et al. |
| 9,695,394 B1 | 7/2017 | Coelho et al. |
| 2002/0107469 A1 | 8/2002 | Bolan et al. |
| 2008/0199949 A1 | 8/2008 | Alroy |
| 2010/0042015 A1 | 2/2010 | Brown |
| 2010/0310588 A1 | 12/2010 | Bluestone et al. |
| 2011/0110909 A1 | 5/2011 | Ildstad et al. |
| 2012/0177621 A1 | 7/2012 | Strober et al. |
| 2012/0329668 A1 | 12/2012 | Sarwal et al. |
| 2014/0004085 A1 | 1/2014 | Kaplan |
| 2014/0369974 A1 | 12/2014 | Reisner et al. |
| 2017/0106086 A1 | 4/2017 | Strober et al. |
| 2018/0221410 A1 | 8/2018 | Strober et al. |

(Continued)

FOREIGN PATENT DOCUMENTS

| | | |
|---|---|---|
| EP | 2606120 B1 | 10/2015 |
| WO | 1995003062 A1 | 2/1995 |

(Continued)

OTHER PUBLICATIONS

Alexander, 2008, Chimerism and Tolerance in a Recipient of a Deceased-Donor Liver Transplant, N Engl J Med, 358:369-74.
Arai, 2015, Increasing Incidence of Chronic Graft-versus-Host Disease in Allogeneic Transplantation: A Report from the Center for International Blood and Marrow Transplant Research, Biol Blood Marrow Transplant, 21:266-274.
Arbab, 2004, Efficient Magnetic Cell Labeling with Protamine Sulfate Complexed to Ferumoxides for Cellular MRI Blood, American Soc. of Hematology, 104(4):1217-1223.
Bakhuraysah, 2016, Hematopoietic stem cell transplantation for multiple sclerosis: is it a clinical reality? Sem Cell Res Ther. 2016; 7:12, 12 pages.
Beelen, 2000, Transplantation of highly purified HLA-identical sibling donor peripheral blood CD34+ cells without prophylactic post-transplant immunosuppression in adult patients with first chronic phase chronic myeloid leukemia: results of a phase II study, Bone Marrow Transplantation, 823-829, 26, Macmillan Publishers Ltd., Basingstoke, United Kingdom.

(Continued)

*Primary Examiner* — Zachary S Skelding
(74) *Attorney, Agent, or Firm* — Brown Rudnick LLP; Adam M. Schoen

(57) ABSTRACT

The invention provides cellular compositions that contain CD34+ cells derived from bone marrow of a decease donor and CD3+ cells derived from non-bone marrow of the deceased donor. The compositions are useful to promote mixed chimerism in recipients of solid organ transplants. The invention also provides methods of making and using such compositions. In certain embodiments, the invention further provides methods of analyzing and preparing blood and blood components from a deceased donor for use in compositions of the invention to promote mixed chimerism in solid organ transplant recipients.

11 Claims, 13 Drawing Sheets

(56) References Cited

U.S. PATENT DOCUMENTS

| | | | |
|---|---|---|---|
| 2019/0307803 A1 | 10/2019 | Deitcher | |
| 2019/0358269 A1 | 11/2019 | Reisner et al. | |
| 2021/0189344 A1* | 6/2021 | Veale | A61K 38/193 |

FOREIGN PATENT DOCUMENTS

| | | |
|---|---|---|
| WO | 2002040640 A2 | 5/2002 |
| WO | 2003012060 A2 | 2/2003 |
| WO | 03101201 A1 | 12/2003 |
| WO | 2011068829 A1 | 6/2011 |
| WO | 2012024427 A2 | 2/2012 |
| WO | 2012096974 A1 | 7/2012 |
| WO | 2013093919 A2 | 6/2013 |
| WO | 2014133729 A1 | 9/2014 |
| WO | 2017/005647 A1 | 1/2017 |

OTHER PUBLICATIONS

Dick, 1997, Assay of human stem cells by repopulation of NOD/SCID mice, Stem Cells, 1997;15 Suppl 1:199-203.
Field, 2001, Tolerance, mixed chimerism and protection against graft-versus-host disease after total lymphoid irradiation, Phil. Trans. R. Soc. Lond. B, 356:739-748.
Frisch, 2014, Hematopoietic Stem Cell Cultures and Assays, Methods Mol Biol. 2014; 1130: 315-324.
Fudaba, 2006, Myeloma Responses and Tolerance Following Combined Kidney and Nonmyeloablative Marrow Transplantation: In Vivo and In Vitro Analyses, American Journal of Transplantation, 6: 2121-2133.
Jun. 2007, Adoptive T cell therapy for cancer in clinic, J Clin Invest, 117(6):1466-76, vol. 117.
Kalwak, 2010, Higher CD34+ and CD3+ Cell Doses in the Graft Promote Long-Term Survival, and Have No Impact in the Incidence of Severe Acute or Chronic Graft-versus-Host Disease after In Vivo T Cell-Depleted Unrelated Donor Hematopoietic Stem Cell Transplantation in Children, Biol Blood Marrow Transplant, 16:1388-1401.
Kawai, 2008, HLA-mismatched Renal Transplantation without Maintenance Immunosuppression, New England Journal of Medicine, 358(4):353-361.
Khalil, 2017, Rubbing Against Blood Clots Uding Helical Robots: Modeling and In Vitro Experimental Validation, IEEE Robotics and Automation Letter vol. 2, No. 2, 927-934.
Kohrt, 2009, TLI and ATG Conditioning with Low Risk of Graft-Versus-Host Disease Retains Antitumor Reactions after Allogeneic Hematopoietic Cell Transplantation from Related and Unrelated Donors, Blood, 114(5):1099-1109.
Ledford, 2008, Organ Transplant without Rejection, Nature News, ISSN 0028-0836, EISSN 1476-4687 (3 pages).
Leventhal, 2012, Chimerism and tolerance without GVHD or engraftment syndrome in HLA-mismatched combined kidney and hematopoietic stem cell transplantation, Sci Transl Med. 4(124):1-22.
Leventhal, 2013, Tolerance Induction in HLA Disparate Living Donor Kidney Transplantation by Donor Stem Cell Infusion: durable chimerism predicts outcome, Transplantation, 95(1):169-176.
Mali, 2013, Delivery systems for gene therapy, Indian J Hum Genet. Jan.-Mar. 2013; 19(1): 3-8, 8 pages.
Milan, 2002, Mixed chimerism and immunosuppressive drug withdrawal after HLA-mismatched kidney and hematopoietic progenitor transplantation, Transplantation, 73:1386-1391.
Ng, 2009, Isolation of human and mouse hematopoietic stem cells, Methods Mol Biol., 506:13-21.
Perez-Pujol, 2005, Proteomic analysis of gray platelet syndrome by iTRAQ Labelling and mass spetroscopy: a potential new diagnostic strategy for platelet disorders, Blood, (ASH Annual Meeting Abstracts), 106(11):2161.
Sachs, 2014,Induction of Tolerance through Mixed Chimerism, Cold Spring Harb Perspect Med, 4;4:a015529, 19 pages.
Scandling, 2008, Tolerance and Chimerism after Renal and Hematopoietic-Cell Transplantation, N Engl J Med, 358:362-8.
Scandling, 2012, Tolerance and withdrawal of immunosuppressive drugs in patients given kidney and hematopoietic cell transplants, Am J Transplant., 12(5):1133-45.
Scandling, 2015, Chimerism, Graft Survival, and Withdrawal of Immunosuppressive Drugs in HLA Matched and Mismatched Patients After Living Donor Kidney and Hematopoietic Cell Transplantation, American Journal of Transplantation, 15:695-704.
Slavin, 1977, Induction of specific tissue transplantation tolerance using fractionated total lymphoid irradiation in adult mice: long-term survival of allogeneic bone marrow and skin grafts, J. Exp. Med., 146:34-48.
Spohn, 2015, Automated CD34+ cell isolation of peripheral blood stem cell apheresis product, Cytotherapy, 10:1465-71.
Stanford Team Prevent Kidney Transplant Rejection Without Drugs, ScienceDaily, Apr. 24, 2002, pp. 1-3, downloaded from www.sciencedaily.com/releases/2002/04/020424072642.htm.
Strober, 2011, Translational studies in hematopoietic cell transplantation: treatment of hematologic malignancies as a stepping stone to tolerance induction, Semin Immunol., 23(4):273-81.
Sykes, 2001, Mixed Chimerism and Transplant Tolerance, Immunity, 14:417-424.
Szabolcs, 2012, Tolerance after solid organ and hematopoietic cell transplantation, Biol Blood Marrow Transplant, 18(1):S193-200.
Tatekawa, 2006, A novel direct competitive repopulation assay for human hematopoietic stem cells using NOD/SCID mice, Cytotherapy, vol. 8, No. 4, 390-398.
Urbano-Ispizua, 2001, The number of donor CD3+ cells is the most important factor for graft failure after allogeneic transplantation of CD34+ selected cells from peripheral blood from HLA-identical siblings, Blood,97(2):383-387.
International Search Report and Written Opinion for International Application No. PCT/US2019/025958, filed Apr. 5, 2019, dated Jul. 2, 2019, 7 pages.
International Search Report and Written Opinion for International Application No. PCT/US2019/051711, filed Sep. 18, 2019, dated Jan. 15, 2020, 9 pages.
Ades, 1989, Cell suspension from collagenase digestion of bone matton trephine biopsy specimens, Journal of Clinical Pathology, 42:427-432.
Czerw, 2016, High CD3+ and CD34+ peripheral blood stem cell grafts content is associated with increased risk of graft-versus-host disease without beneficial effect on disease control after reduced-intensity conditioning allogeneic transplantation from matched unrelated donors for acute myeloid leukemia, Oncotarget, 7(19):27255-27266.
Extended European Search Report issued in European Application No. 19781109.4, dated Feb. 17, 2022, 6 pages.
Extended European Search Report issued in European Application No. 19782310.7, dated Feb. 17, 2022, 7 pages.
Extended European Search Report issued in European Application No. 19861568.4, dated Jun. 1, 2022, 7 pages.
Hildebrandt, 2000, Immunomagnetic selection of CD34 + cells: factors influencing component purity and yield, Transfusion, 40:507-512.
Ispzua, 2001, The Number of Donor CD3+ Cells is the Most Important Factor, Blood, 97(2):383-387.
Kalwak, 2010, Higher CD34+ and CD3+ Cell Doses, Biol Blood Marrow Transplant, 16:1388-1401.
Konieczna, 2013, Human Immunology, Abstracts, 74:1-49, 35-OR, 1 page.
Link, 1995, Combined transplantation of allogeneic bone marrow and CD34+ blood cells, 86(7):2500-2508.
Matthew, 1998, Cellular immune responses of human cadaver donor bone marrow cells and their susceptibility to commonly used immunosuppressive drugs in transplantation, Transplantation, 66(7):947-955.
Shapiro, 2017, Bone Marrow aspiration for regenerative orthopedic intervention: technique with ultrasound guidance for needle placement. Methodology, 12:8, 917-928.

(56) References Cited

OTHER PUBLICATIONS

Yu, 2016, G-CSF and hypoxic conditioning improve the proliferation, neural differentiation and migration of canine bone marrow mesenchymal stem cells, Experimental and Therapeutic Medicine, 12:1822-1828.

Zeng, 2002, Unique patterns of surface receptors, cytokine secretion, and immune functions distinguish T cells in the bone marrow from those in the periphery: impact on allogenic bone marrow transplantation, Blood, 99 (4):1449-1457.

Zuber, 2017, Mechanisms of Mixed Chimerism-Based Transplant Tolerance, Trends In Immunology, 38(11):829-843.

* cited by examiner

CELLULAR COMPOSITIONS DERIVED FROM DECEASED DONORS TO PROMOTE GRAFT TOLERANCE AND MANUFACTURE AND USES THEREOF

CROSS-REFERENCE TO RELATED APPLICATION

This application claims the benefit of, and priority to, U.S. Provisional Application No. 62/732,823, filed Sep. 18, 2018, the contents of which are incorporate herein by reference.

FIELD OF THE INVENTION

The invention generally relates to therapeutic compositions comprising cells derived from deceased donors and methods of manufacturing and using the same.

BACKGROUND

Nearly 35,000 organ transplants are performed in the United States each year. The primary complication of organ transplantation is rejection of the organ by the recipient's immune system. To avoid organ rejection, most transplant recipients must take immunosuppressive drugs for the rest of their lives. Immunosuppressive therapy, however, carries its own set of risks, including increased risk of infection, cancer, hypertension, and liver damage. In addition, immunosuppression does not guarantee that the recipient will tolerate the graft.

Long-term graft tolerance without immunosuppression can be achieved by reconstruction of the recipient's immune system to comprise a mixture of donor-derived and recipient-derived cells, a state called mixed chimerism. Accordingly, establishing mixed chimerism in organ transplant recipients has become very desirable.

Mixed chimerism can be achieved by providing the recipient with donor blood cells, including hematopoietic stem and progenitor cells (HSPCs) and T cells. Unfortunately, the supply of blood cells from adult donors is limited by the difficulties of obtaining HSPCs from living donors. HSPCs may be collected from living donors by surgical extraction, but surgery typically involves general anesthesia, can be painful, and carries a risk of infection or damage to nerves and muscles. Alternatively, HSPCs can be recovered non-surgically by administering to the donor an agent that mobilizes HSPCs from the bone marrow into the blood and collecting cells from peripheral blood by apheresis. However, apheresis can take up to six hours, may need to be repeated for several days to obtain a sufficient quantity of HSPCs, and poses a risk of infection and blood clotting. Furthermore, regardless of the method, donation of HSPCs provides no medical benefit to the donor, so many individuals are unwilling to donate HSPCs unless they have a direct familial or personal relationship with the recipient.

SUMMARY

The invention recognizes that deceased donors represent a potential alternative source of HSPCs and T cells, and the invention provides various approaches and techniques that address challenges associated with obtaining these therapeutically useful cells from deceased donors. Particularly, the invention takes advantage of numerous different insights and discoveries associated with working with a deceased donor's tissues and body fluids, which are leveraged herein to develop new manufacturing processes for production of new engineered hematopoietic cellular products derived from deceased donors. For example, new techniques, products, and approaches have been developed, which include, but are not limited to, new blood collection apparatuses for collecting blood from a deceased donor, new methods for ex vivo extraction of $CD34^+$ cells from bone marrow of a deceased donor, new methods for processing deceased donor blood, and development of new assays for analyzing deceased donor blood. All of these insights and developments have resulted in new manufacturing processes for production of new engineered hematopoietic cellular products derived from deceased donors.

In certain aspects, the invention provides new cellular compositions that include HSPCs derived from bone marrow of a deceased donor and T cells derived from non-bone marrow of the deceased donor. Compositions that include $CD3^+$ T cell derived from non-bone marrow of a deceased donor (e.g., blood of the deceased donor) have never been previously possible, until development of the manufacturing processes described herein. In certain embodiments, bone marrow-derived HSPCs are identified by expression of CD34, and T cells are identified by expression of CD3. The cellular compositions contain $CD34^+$ cells and $CD3^+$ cells in quantities sufficient to promote establishment of mixed chimerism in recipients of solid organ transplants.

The compositions and methods of the invention greatly improve the utility of stem cell transfer to support organ transplantation. First, they avoid the need to obtain HSPCs from living individuals, who are often reluctant to endure the side effects of donation procedures from which they receive no medical benefit. At the same time, the compositions and methods provided herein overcome several of the problems associated with obtaining HSPCs and T cells from deceased donors. Significantly, because different sources are used to obtain $CD34^+$ cells and $CD3^+$ cells, the yield of each cell type is optimized. For example, rich bone marrow sources, such as the iliac crest or vertebral bodies, serve as the source of $CD34^+$ cells, whereas $CD3^+$ cells are obtained from blood. Separate processing of HSPCs and T cells also allows different sources to be subjected to specific protocols that facilitate isolation and preserve functionality of a particular cell population. For example, bone marrow may be treated with agents, such as granulocyte colony stimulating factor (G-CSF), that mobilize HSPCs but may not be beneficial for T cells. The invention also provides methods of analysis of HSPCs and T cells obtained from deceased donors to ensure that populations of such cells are suitable for use in making cellular products to administer to living recipients.

In another aspect, the invention provides cellular products for establishing mixed chimerism in a solid organ transplant recipient. The products include greater than $1 \times 10^5$ $CD34^+$ cells/kg recipient weight derived from bone marrow of a deceased donor and greater than $1 \times 10^5$ $CD3^+$ cells/kg recipient weight derived from non-bone marrow (e.g., blood) of the deceased donor.

In another aspect, the invention provides methods for establishing mixed chimerism in a solid organ transplant recipient. The methods include providing to a subject that has received or will receive a solid organ transplant a product containing greater than $1 \times 10^5$ $CD34^+$ cells/kg recipient weight derived from bone marrow of a deceased donor and greater than $1 \times 10^5$ $CD3^+$ cells/kg recipient weight derived from non-bone marrow of the deceased donor.

The cellular products may include various amounts of each of the $CD34^+$ cells and $CD3^+$ cells. The amount may be specified as a number of cells relative to the body mass of the recipient. For example, the cellular product may contain at least $1\times10^5$, $2\times10^5$, $5\times10^5$, $1\times10^6$, $2\times10^6$, $4\times10^6$, $1\times10^7$, $2\times10^7$, $4\times10^7$, $1\times10^8$, $2\times10^8$, or $5\times10^8$ CD34$^+$ cells/kg recipient weight. The cellular product may contain at least $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, $1\times10^8$, $2\times10^8$, or $5\times10^8$ CD3$^+$ cells/kg recipient weight.

The cellular product may contain at least $1\times10^5$ CD34$^+$ cells/kg recipient weight, at least $2\times10^5$ CD34$^+$ cells/kg recipient weight, at least $4\times10^5$ CD34$^+$ cells/kg recipient weight, at least $5\times10^5$ CD34$^+$ cells/kg recipient weight, at least $1\times10^6$ CD34$^+$ cells/kg recipient weight, at least $2\times10^6$ CD34$^+$ cells/kg recipient weight, at least $4\times10^6$ CD34$^+$ cells/kg recipient weight, at least $5\times10^6$ CD34$^+$ cells/kg recipient weight, at least $1\times10^7$ CD34$^+$ cells/kg recipient weight, at least $2\times10^7$ CD34$^+$ cells/kg recipient weight, at least $4\times10^7$ CD34$^+$ cells/kg recipient weight, at least $1\times10^8$ CD34$^+$ cells/kg recipient weight, at least $2\times10^8$ CD34$^+$ cells/kg recipient weight, at least $4\times10^5$ CD34$^+$ cells/kg recipient weight, or at least $5\times10^8$ CD34$^+$ cells/kg recipient weight. The cellular product may contain at least $1\times10^5$ CD3$^+$ cells/kg recipient weight, at least $2\times10^5$ CD3$^+$ cells/kg recipient weight, at least $4\times10^5$ CD3$^+$ cells/kg recipient weight, at least $5\times10^5$ CD3$^+$ cells/kg recipient weight, at least $1\times10^6$ CD3$^+$ cells/kg recipient weight, at least $2\times10^6$ CD3$^+$ cells/kg recipient weight, at least $4\times10^6$ CD3$^+$ cells/kg recipient weight, at least $5\times10^6$ CD3$^+$ cells/kg recipient weight, at least $1\times10^7$ CD3$^+$ cells/kg recipient weight, at least $2\times10^7$ CD3$^+$ cells/kg recipient weight, at least $4\times10^7$ CD3$^+$ cells/kg recipient weight, at least $1\times10^8$ CD3$^+$ cells/kg recipient weight, at least $2\times10^8$ CD3$^+$ cells/kg recipient weight, at least $4\times10^5$ CD3$^+$ cells/kg recipient weight, or at least $5\times10^8$ CD3$^+$ cells/kg recipient weight. The cellular product may contain about $1\times10^5$ CD3$^+$ cells/kg recipient weight, about $2\times10^5$ CD3$^+$ cells/kg recipient weight, about $4\times10^5$ CD3$^+$ cells/kg recipient weight, about $5\times10^5$ CD3$^+$ cells/kg recipient weight, about $1\times10^6$ CD3$^+$ cells/kg recipient weight, about $2\times10^6$ CD3$^+$ cells/kg recipient weight, about $4\times10^6$ CD3$^+$ cells/kg recipient weight, about $5\times10^6$ CD3$^+$ cells/kg recipient weight, about $1\times10^7$ CD3$^+$ cells/kg recipient weight, about $2\times10^7$ CD3$^+$ cells/kg recipient weight, about $4\times10^7$ CD3$^+$ cells/kg recipient weight, about $1\times10^8$ CD3$^+$ cells/kg recipient weight, about $2\times10^8$ CD3$^+$ cells/kg recipient weight, about $4\times10^5$ CD3$^+$ cells/kg recipient weight, or about $5\times10^8$ CD3$^+$ cells/kg recipient weight.

The bone marrow may be derived from any bone source. For example, the bone may be derived from iliac crests or vertebral bodies.

The non-bone marrow may be any tissue or fluid that is not bone marrow. For example, the non-bone marrow may be blood, liver, lymph nodes, spleen, or thymus. Preferably, the non-bone marrow is blood.

The deceased donor may be an adult, child, or fetus.

The CD34$^+$ cells, the CD3$^+$ cells, or both may be HLA-matched to the solid organ transplant recipient. The CD34$^+$ cells, the CD3$^+$ cells, or both may be HLA-mismatched to the solid organ transplant recipient. The donor and recipient may be HLA-matched at six, eight, ten, or twelve alleles among the HLA-A, HLA-B, HLA-C, HLA-DP, HLA-DQ, and HLA-DR genes. The donor and recipient may be HLA-mismatched at one, two, three, four, five, six, or more alleles among the HLA-A, HLA-B, HLA-C, HLA-DP, HLA-DQ, and HLA-DR genes.

The CD34$^+$ cells and the CD3$^+$ cells may be provided in separate containers. The CD34$^+$ cells and the CD3$^+$ cells may be provided as a mixture in one or more common containers.

The cellular products may contain a cryopreservation medium. The cryopreservation medium may contain a cryoprotectant, such as DMSO or dextran having a molecular weight of about 40,000 Da. The cryoprotectant may be present at a concentration of about 1%, 2%, 3%, 4%, 5%, 7.5%, or 10%.

The solid organ may be any solid organ that can be transplanted according to methods known in the art. For example and without limitation, the solid organ may be a kidney, lung, pancreas, pancreatic islet cells, heart, intestine, colon, liver, skin, muscle, gum, eye, or tooth. Preferably, the solid organ is a kidney.

In other aspects, the invention provides methods of preparing a cellular product for establishing mixed chimerism in a solid organ transplant recipient. The methods include obtaining CD34$^+$ cells derived from bone marrow of a deceased donor, obtaining CD3$^+$ cells derived from non-bone marrow of the deceased donor, and producing a cellular product including the obtained CD34$^+$ cells and the obtained CD3$^+$ cells for administration to a solid organ transplant recipient. The cellular product may include one or more features described above. In certain embodiments, the non-bone marrow may be blood, liver, lymph nodes, spleen, or thymus. Preferably, the non-bone marrow is blood.

The methods may include exsanguinating the deceased donor before CD34$^+$ cells are obtained from bone marrow. The methods may include removing bone marrow from a portion of bone of the deceased donor. For example, the bone marrow may be removed by aspiration or trephination. Methods involving trephination may include one or more additional steps to separate bone marrow from bone shards. For example and without limitation, bone marrow may be separated from bone shards by one or more of agitation, enzymatic disaggregation, washing, and filtration.

The methods may include treating the bone marrow with an anticoagulant. For example and without limitation, the anticoagulant may be acenocoumarol, antithrombin III, apixaban, argatroban, atromentin, betrixaban, bivalirudin, brodifacoum, dabigatran, dalteparin, difenacoum, edoxaban, EDTA, enoxaparin, fondaparinux, heparin, idraparinux, phenindione, phenprocoumon, rivaroxaban, or warfarin. The bone marrow may be treated with an anticoagulant prior to its removal from the portion of bone, or it may be treated with an anticoagulant after its removal from the portion of bone.

The methods may include treating the bone marrow with an agent that mobilizes CD34$^+$ cells from bone marrow. For example and without limitation, the agent that mobilizes CD34$^+$ cells from bone marrow may be an adenosine receptor antagonist, BIO5192, a CCR1 antagonist, a CCR2 antagonist, a CXCR2 antagonist, a CXCR4 antagonist, cyclophosphamide, defibrotide, EphA3-Fc, erythropoietin (EPO), glycosaminoglycan (GAG) mimetic, granulocyte colony stimulating factor (G-CSF), granulocyte macrophage colony stimulating factor (GM-CSF), growth-regulated oncogene beta (GRO-beta), human growth hormone, IL-8, macrophage inflammatory protein-1 alpha (MIP-1 alpha), met-SDF-1 k beta, NSC23766, parathyroid hormone, pertussis toxin, plerixafor, a poly-[1-6]-D-glucopyranosyl-[1-3]-D-glucopyranose (PGG) glucan, a Rac1 inhibitor, a retinoic acid receptor agonist, SB290157, a SDF-1 alpha peptide analog, stem cell factor (SCF), sulfated colominic acid, a sulfated polysaccharide, T134, T140, thrombopoietin (TPO), a TPO receptor agonist, a VCAM-1 inhibitor a VLA-1 inhibitor, a VLA-4 inhibitor, or an analog or derivative of any of the aforementioned. The bone marrow may be treated with an agent that mobilizes CD34$^+$ cells from bone marrow prior to its removal from the portion of bone, or it may be treated with an agent that mobilizes CD34+ cells from bone marrow after its removal from the portion of bone.

Obtaining CD34+ cells may include depleting the bone marrow of red blood cells, platelets, or both. For example and without limitation, the bone marrow may be depleted of red blood cells and/or platelets by buoyancy-activated cell separation, cell lysis, hetastarch sedimentation, immunomagnetic depletion, size-based centrifugal separation, or spinning membrane filtration. The bone marrow may be depleted of red blood cells and/or platelets prior to its removal from the portion of bone, or it may be depleted of red blood cells and/or platelets after its removal from the portion of bone.

Obtaining CD34+ cells may include immunoselecting CD34+ cells from the removed bone marrow. Preferably, CD34+ cells are immunoselected after removal of the bone marrow from the portion of bone.

Obtaining CD3+ cells may include depleting the non-bone marrow, e.g., blood, of red blood cells, platelets, or both. For example and without limitation, the bone marrow may be depleted of red blood cells and/or platelets by buoyancy-activated cell separation, cell lysis, hetastarch sedimentation, immunomagnetic depletion, size-based centrifugal separation, or spinning membrane filtration.

Obtaining CD3+ cells may include other methods of enriching the non-bone marrow for CD3+ cells. The methods may include positive selection of CD3+ cells, depletion of non-CD3+ cells, or a combination thereof. Positive selection of CD3+ cells may include binding of one or more markers on CD3+ cells using a binding agent fixed to a solid substrate. Depletion of non-CD3+ cells may include binding of one or more markers absent from CD3+ cells using a binding agent fixed to a solid substrate. Markers for positive selection of CD3+ cells may include one or more of CD3, CD4, and CD8. Markers for negative selection of CD3+ cells may include one or more of CD10, CD14, CD15, CD33, CD41, CD71, CD209, and CD235. The binding agent may be an antibody. The solid substrate may be a bead or particle. Obtaining CD3+ cells may include preventing and/or removing clots, cell clumps, or both from the non-bone marrow, e.g., blood. Removal of clots and/or clumps may include filtration, e.g., filtration of blood or treating blood with an anticoagulant.

Obtaining CD3+ cells may include separating blood into a cellular fraction and a plasma fraction.

The methods may include combining the obtained CD34+ cells and the obtained CD3+ cells. Alternatively, the methods may include storing the obtained CD34+ cells and the obtained CD3+ cells in separate containers.

The methods may include cryopreserving the obtained CD34+ cells and the obtained CD3+ cells. For example, the cells may be cryopreserved by addition of a cryoprotectant, such as DMSO or dextran having a molecular weight of about 40,000 Da.

In another aspect, the invention provides methods of creating a cellular product from hematopoietic cells obtained from bone marrow ex vivo. The methods include obtaining a sample comprising bone marrow from a subject's body, obtaining hematopoietic cells from the sample after the sample has been removed from the subject's body, and producing a cellular product containing the hematopoietic cells for administration to a solid organ transplant recipient.

Preferably, the subject is deceased when the sample is obtained from the subject's body. The subject may be any mammal, such as a human or primate. Preferably, the subject is human.

The sample may be obtained from any bone in the subject's body. Preferably, the sample is obtained from iliac crests or vertebral bodies, or both.

The hematopoietic cells may be a subset of hematopoietic cells that express one or more markers. For example and without limitation, the hematopoietic cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells ($T_{SCM}$), naïve T cells, cytotoxic T cells, gamma delta T cells, natural killer T cells, CD34+ cells, CD4+ cells, or CD3+ cells.

Hematopoietic cells may be obtained from the sample by any suitable means. For example and without limitation, hematopoietic cells may be obtained by removing bone marrow from the sample by aspiration or trephination. Methods involving trephination may include one or more additional steps to separate bone marrow from bone shards, such as those described above. Hematopoietic cells may be obtained by contacting the sample with an agent that mobilizes be CD34+ cells from bone marrow, such as one or more of the agents described above.

Bone marrow removed from the sample may be further processed. For example, bone marrow may be treated with an anticoagulant, such as one described above. Bone marrow cells may be separated from bone shards, for example, by a method described above. Bone marrow may be depleted of red blood cells, platelets, or both, for example, by a method described above. CD34+ cells may be immunoselected from the bone marrow.

The methods may include cryopreserving the cellular product. The cellular product may be cryopreserved using a cryoprotectant, such as one described above.

The cellular product may provide a therapeutic benefit to the solid organ transplant recipient. For example, the cellular product may promote establishment of mixed chimerism in a solid organ transplant recipient.

The solid organ may be any solid organ, such as one of those described above.

The hematopoietic cells may be HLA-matched or HLA-mismatched to the solid organ transplant recipient, as described above in relation to cellular products containing CD34+ cells and CD3+ cells.

In another aspect, the invention provides methods of assessing whether blood derived from a deceased donor is suitable for use in manufacture of a product to administer to a living recipient. The methods include obtaining blood from a deceased donor, analyzing a component of the blood, and determining, based on analysis of the component, whether the blood is suitable for use in manufacture of a product to administer to a living recipient.

In another aspect, the invention provides methods of assessing whether blood derived from a deceased donor is suitable for use in manufacture of a product to administer to a living recipient. The methods include obtaining blood from a deceased donor, analyzing a component of a non-blood tissue from the deceased donor, and determining, based on analysis of the component, whether the blood is suitable for use in manufacture of a product to administer to a living recipient.

The non-blood tissue may be bone marrow, spleen, liver, lymph nodes, or thymus.

The methods may include analysis of multiple components. The methods may include analysis of multiple blood components, multiple components from non-blood tissue, or at least one blood component and at least one component from non-blood tissue.

The component of blood or non-blood tissue may be a cell type or population of cells. For example and without limitation, the cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, $CD34^+$ cells, $CD4^+$ cells, or $CD3^+$ cells.

The component of blood or non-blood tissue may be a non-cellular component, such as a molecule. For example and without limitation, the molecule may be a cytokine, a pro-inflammatory cytokine, an anti-inflammatory cytokine, a chemokine, an antibody, or an immunoglobulin.

The suitability of blood for use in manufacture of a product to administer to a living recipient may include analysis of T cells. For example and without limitation, one or more of T cell activation, exhaustion, anergy, proliferation, viability, and apoptosis may be analyzed. Analysis of one or more of T cell activation, exhaustion, and anergy may include detection of one or more markers or receptors on the surface of T cells.

The suitability of blood for use in manufacture of a product to administer to a living recipient may include analysis of HSPCs. For example and without limitation, one or more of HSPC proliferation, HSPC viability, and HSPC apoptosis may be analyzed. HSPC proliferation and/or viability may be assayed in colony-forming, long-term culture, or mouse model repopulation assays.

The suitability of blood for use in manufacture of a product to administer to a living recipient may include analysis of levels of cytokines or chemokines.

Analysis of a component of blood or a non-blood tissue from a deceased donor may include comparison to the same component from a living donor.

The methods may include using material from the blood in the manufacture of the product if the blood is determined to be suitable for such use. The material from the blood may be a cell type or population of cells. For example and without limitation, the cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, $CD34^+$ cells, $CD4^+$ cells, or $CD3^+$ cells. The material from the blood may be a non-cellular component, such as a molecule. For example and without limitation, the molecule may be a cytokine, chemokine, antibody, or immunoglobulin. The methods may include using multiple materials from the blood in the manufacture of the product.

The methods may include expansion of cellular material for use in manufacture of the product.

The methods may include treating the blood to minimize or mitigate damage to material in the blood that may be used in manufacture of the product.

In an aspect, the invention provides multiple cellular products derived from a single deceased donor for establishing mixed chimerism in multiple solid organ transplant recipients. Each product includes greater than $1\times10^5$ $CD34^+$ cells/kg recipient weight and greater than $1\times10^5$ $CD3^+$ cells/kg recipient weight, and multiple products are derived from a single deceased donor. The $CD34^+$ cells are derived from bone marrow, and the $CD3^+$ cells are derived from non-bone marrow. The cellular products may include any of the features of the cellular products described above.

In another aspect, the invention provides methods for establishing mixed chimerism in multiple solid organ transplant recipients. The methods include providing to each of multiple subjects that have received or will receive a solid organ transplant a product containing greater than $1\times10^5$ $CD34^+$ cells/kg recipient weight and greater than $1\times10^5$ $CD3^+$ cells/kg recipient weight. The $CD34^+$ cells of each product are derived from the bone marrow of one deceased donor, and the $CD3^+$ cells of each product are derived from non-bone marrow of the deceased donor. The methods may include any of the features described above in relation to methods for establish mixed chimerism in a solid organ transplant recipient.

Each product may contain at least $1\times10^5$, $2\times10^5$, $5\times10^5$, $1\times10^6$, $2\times10^6$, $4\times10^6$, $1\times10^7$, $2\times10^7$, $4\times10^7$, $1\times10^8$, $2\times10^8$, or $5\times10^8$ $CD34^+$ cells/kg recipient weight. Each product may contain at least $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $4\times10^7$, $1\times10^8$, $2\times10^8$, or $5\times10^8$ $CD3^+$ cells/kg recipient weight.

In an aspect, the invention provide methods of separating the blood from a deceased donor into a cellular component and a non-cellular component and using material in the cellular component to produce a product for establishing mixed chimerism in a solid organ transplant recipient. The product may have any feature of the cellular products described above.

The methods may involve treating the blood or a component of the blood with an anticoagulant, such as one described above. Treatment with anticoagulant may occur prior to separation of the blood into a cellular component and a non-cellular component, or it may occur after separation.

The methods may involve depleting the blood or a component of the blood of red blood cells, platelets, or both. Depletion of red blood cells and/or platelets may be performed by any method described above. Depletion of red blood cells and/or platelets may be performed prior to separation of the blood into a cellular component and a non-cellular component, or it may occur after separation.

The methods may involve removing clots and/or clumps from the blood or a component of the blood. Clots and/or clumps may be removed by any method described above. Clots and/or clumps may be removed prior to separation of the blood into a cellular component and a non-cellular component, or they may be removed after separation.

The methods may include enriching the blood or a component of the blood for a particular type of hematopoietic cell, such as B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, $CD34^+$ cells, $CD4^+$ cells, or $CD3^+$ cells. One or more cell types may be enriched by immunoselection.

The methods may include analysis of the blood or a component of the blood by any method described above. The methods may include determining whether the blood or a component of the blood is suitable for use in manufacture of a product to administer to a living recipient or a product for establishing mixed chimerism in a solid organ transplant recipient.

The methods may include expansion of a cellular component of the blood.

In another aspect, the invention provides devices for collection of blood from a deceased donor. In certain embodiments, the devices include one or more receptacles coupled to a cooling system.

The device may have 1, 2, 3, 4, 5, 6, 7, 8, 9, 10, or more receptacles. Preferably, the receptacles have a combined capacity of from about 5 to about 10 liters. For example, each receptacle may have capacity of about 0.5, 1, 2, 3, 4, 5, 6, 7, 8, 9, or 10 liters.

The cooling system is configured to cool blood in the receptacles to a target temperature. The target temperature may from about 2° C. to about 8° C. The cooling system may prevent blood from freezing or formation of ice crystals within the blood. The cooling system may cool blood to the target temperature within a period of time. For example, the cooling system may cool blood to the target temperature in about 4 hours, about 5 hours, about 6 hours, about 7 hours, about 8 hours, about 9 hours, about 10 hours, not less than 4 hours, not less than 5 hours, not less than 6 hours, not less than 7 hours, not less than 8 hours, not more than 6 hours, not more than 7 hours, not more than 8 hours, not more than 9 hours, or not more than 10 hours.

The device may include a needle coupled to the one or more receptacles. The needle may be coupled to the one or more receptacles by tubing.

The device may include a vacuum system configured to apply a vacuum to remove blood from the deceased donor. The vacuum system may be coupled to one or more of the needle, tubing, and receptacle.

In an aspect, the invention provides methods of collecting blood from a deceased donor for use in manufacture of products for transfer to a living recipient. The methods may include transferring blood to a device that includes one or more receptacles coupled to a cooling system. The device may include any of the features described above.

The methods may include inserting a needle into a blood vessel, artery, or vein of the deceased donor. The methods may include applying a vacuum to the blood vessel, artery, or vein of the deceased donor.

The methods may include contacting the blood with a stabilizing agent. The stabilizing agent may an anticoagulant, such as one described above, or an osmotic stabilizing agent, such as human serum albumin.

The methods may include contacting the blood with a cryoprotectant, such as one described above.

DETAILED DESCRIPTION

Figure 1:
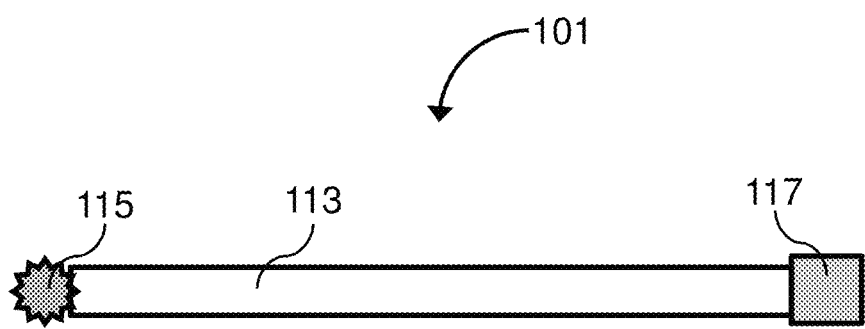
FIG. 1 is an illustration of the external cortical cutting trocar of a marrow extracting device according to an embodiment of the invention.

The primary hurdle to overcome in organ transplantation is causing the recipient's immune system to tolerate the donor's tissue. If the recipient's immune system detects the donated organ as foreign, it attacks the tissue, leading to graft rejection. To avoid graft rejection, most transplant recipients must take drugs that suppress the immune system, but such drugs increase the recipient's risk of infection and cancer. As another means to prevent graft rejection, transplantation of solid organs may be accompanied by transfer of donor-derived blood cell progenitors. Providing donor blood cells allows reconstitution of the recipient's immune system to include cells that have been educated to recognize the organ as non-foreign tissue. Consequently, the donated organ is not attacked, and the recipient tolerates the graft.

One strategy for reconstructing the recipient's immune system entails complete replacement of the recipient's hematopoietic system with exclusively donor-derived cells to achieve a state of full chimerism. A risk associated with full chimerism, however, is that the completely donor-derived immune system may identify the recipient's tissue as foreign and attack it, a condition called graft-versus-host disease (GVHD). See, e.g., Sach et al., Induction of Tolerance through Mixed Chimerism, Cold Spring Harb Perspect Med 2014; 4:a015529, doi: 10.1101/cshperspect.a015529, the contents of which are incorporated herein by reference. As a result, fully chimeric patients must remain on immunosuppressive therapy indefinitely.

Another strategy is to repopulate the recipient's immune system with a mixture of donor-derived cells and recipient-derived cells to attain a state called mixed chimerism. Compared to full chimerism, mixed chimerism is associated with lower rates of GVHD. In addition, mixed chimeric regimens require lower doses of immunosuppressive therapy initially and allow complete discontinuation of immunosuppression after the stability of the recipient's mixed chimerism has been established. To date, induction of mixed chimerism is the only method of producing graft tolerance in humans without maintaining immunosuppressive therapy.

Current methods of establishing mixed chimerism require transfer of two different populations of hematopoietic cells from the donor. Mature T cells recognize the transplanted organ as "self" tissue and prevent the immune system from attacking it. Mature T cells express the cell-surface marker CD3, and different sub-populations may be found in the blood and lymph nodes. Although $CD3^+$ T cells promote tolerance upon transfer, they have a finite lifespan and are unable to regenerate themselves. Consequently, transfer of hematopoietic stem and progenitor cells (HSPCs), pluripotent cells that can differentiate into T cells, is also necessary to allow continual replenishment of the donor-derived T cell population. HSPCs express the cell-surface marker CD34 and reside primarily in the bone marrow.

The sacrifice a living donor must make to support long-term graft tolerance in a transplant recipient without lifelong immunosuppressive therapy is substantial. Thus, a living donor must be highly motivated by altruism to undertake the procedures necessary to provide the tissues and cells necessary to support immunosuppression-free graft tolerance. Consequently, few individuals are willing to become living donors of solid organs and hematopoietic cells, particularly if they have no familial or personal relationship with the prospective recipient.

By comparison, a much higher percentage of individuals are willing to donate organs and blood cells posthumously. However, obtaining hematopoietic cells suitable for transfer to a living recipient is more challenging when the donor is deceased. For example, tissues must be removed expeditiously from deceased donors to avoid the detrimental effects of cytokines released during the brain death process. However, HSPCs must be taken from bone marrow of most deceased donors, whereas blood is the best source of T cells. Thus, three types of tissue or fluid must be harvested from the deceased donor: the solid organ of primary interest, blood, and bone marrow. Moreover, the three sources of cellular material must be removed from the body in a sequence that best preserves the functionality of each while ensuring that the entire procedure is completed as quickly as possible.

Another issue with using hematopoietic cells from deceased donors is that the suitability of such cells for transfer into living patients is uncertain. For T cells, the states of activation, exhaustion, and anergy of the cells influence whether the cells are able to promote graft tolerance in a recipient, and these characteristics may vary depending on the donor's cause of death, premortem health, age, sex, lifestyle, and other factors. Cell viability, proliferative potential, and apoptotic state are critical variables in determining the usefulness of both HSPCs and T cells in products to promote mixed chimerism in a recipient.

The invention provides preparative and analytical methods that overcome the difficulties of obtaining hematopoietic cells from deceased donors and using the cells to make compositions suitable for transfer into living recipients. The compositions of the invention promote establishment of mixed chimerism in solid organ transplant recipients and therefore allow such recipients to develop long-term graft tolerance without immunosuppressive therapy.

Consequently, the invention unlocks the therapeutic potential of tissue donated from deceased donors to extend and improve the lives of patients who need organ transplants.

Cellular Products Derived from Deceased Donors for Transfer to Living Recipients The invention provides cellular products that contain hematopoietic cells obtained from deceased donors. All hematopoietic cells are derived from HSPCs, multipotent cells that can differentiate into various specialized cells and also reproduce to generate new HSPCs. HSPCs that differentiate form either lymphoid progenitors or myeloid progenitors. Lymphoid progenitors give rise to lymphocytes and natural killer cells. Myeloid progenitors produce cells of the myeloid and erythroid lineages, such as erythrocytes, platelets, basophils, neutrophils, eosinophils, monocytes, macrophages, and antigen-presenting cells, such as dendritic cells. In adults, most hematopoietic development occurs in the bone marrow, although maturation and activation of some lymphoid cells occurs in the spleen, thymus, and lymph nodes.

The cellular compositions of the invention include two populations of cells that allow donor HSPCs to develop into mature cells of the immune system in the recipient's body. One population includes $CD34^+$ cells. CD34 is a cell surface marker that is expressed in stem cells and their immediate descendants, multipotent progenitor cells, which have not committed to either the myeloid or lymphoid lineage. Consequently, CD34 expression is a useful measure for identifying populations of cells that contain HSPCs. In adults, $CD34^+$ cells reside predominantly in the bone marrow.

The cellular compositions of the invention also include $CD3^+$ cells. CD3 comprises a group of polypeptides that interact with the two polypeptide chains of the T cell receptor to form the T cell receptor complex. The CD3 complex includes a gamma chain, delta chain, and two epsilon chains. CD3 is expressed on the surface of mature T cells and is thus useful as a marker for T cells. $CD3^+$ cells are abundant in the circulating blood.

To promote establishment of mixed chimerism in the recipient, the cellular products include $CD34^+$ cells and $CD3^+$ cells in appropriate quantities. The cellular products may contain $CD34^+$ cells and $CD3^+$ cells in defined amounts. A useful unit of cell quantity in a product is the number of cells relative to the body mass of the recipient. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, or $4\times10^6$, $1\times10^7$, $2\times10^7$, $4\times10^7$, $1\times10^8$, $2\times10^8$, or $5\times10^8$ $CD34^+$ cells/kg recipient weight. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, $1\times10^8$ $CD3^+$, $2\times10^8$, or $5\times10^8$ cells/kg recipient weight.

The cellular product may contain at least $1\times10^5$ $CD34^+$ cells/kg recipient weight, at least $2\times10^5$ $CD34^+$ cells/kg recipient weight, at least $4\times10^5$ $CD34^+$ cells/kg recipient weight, at least $5\times10^5$ $CD34^+$ cells/kg recipient weight, at least $1\times10^6$ $CD34^+$ cells/kg recipient weight, at least $2\times10^6$ $CD34^+$ cells/kg recipient weight, at least $4\times10^6$ $CD34^+$ cells/kg recipient weight, at least $5\times10^6$ $CD34^+$ cells/kg recipient weight, at least $1\times10^7$ $CD34^+$ cells/kg recipient weight, at least $2\times10^7$ $CD34^+$ cells/kg recipient weight, at least $4\times10^7$ $CD34^+$ cells/kg recipient weight, at least $1\times10^8$ $CD34^+$ cells/kg recipient weight, at least $2\times10^8$ $CD34^+$ cells/kg recipient weight, at least $4\times10^5$ $CD34^+$ cells/kg recipient weight, or at least $5\times10^8$ $CD34^+$ cells/kg recipient weight. The cellular product may contain at least $1\times10^5$ $CD3^+$ cells/kg recipient weight, at least $2\times10^5$ $CD3^+$ cells/kg recipient weight, at least $4\times10^5$ $CD3^+$ cells/kg recipient weight, at least $5\times10^5$ $CD3^+$ cells/kg recipient weight, at least $1\times10^6$ $CD3^+$ cells/kg recipient weight, at least $2\times10^6$ CD3⁺ cells/kg recipient weight, at least 4×10⁶ CD3⁺ cells/kg recipient weight, at least 5×10⁶ CD3⁺ cells/kg recipient weight, at least 1×10⁷ CD3⁺ cells/kg recipient weight, at least 2×10⁷ CD3⁺ cells/kg recipient weight, at least 4×10⁷ CD3⁺ cells/kg recipient weight, at least 1×10⁸ CD3⁺ cells/kg recipient weight, at least 2×10⁸ CD3⁺ cells/kg recipient weight, at least 4×10⁵ CD3⁺ cells/kg recipient weight, or at least 5×10⁸ CD3⁺ cells/kg recipient weight. The cellular product may contain about 1×10⁵ CD3⁺ cells/kg recipient weight, about 2×10⁵ CD3⁺ cells/kg recipient weight, about 4×10⁵ CD3⁺ cells/kg recipient weight, about 5×10⁵ CD3⁺ cells/kg recipient weight, about 1×10⁶ CD3⁺ cells/kg recipient weight, about 2×10⁶ CD3⁺ cells/kg recipient weight, about 4×10⁶ CD3⁺ cells/kg recipient weight, about 5×10⁶ CD3⁺ cells/kg recipient weight, about 1×10⁷ CD3⁺ cells/kg recipient weight, about 2×10⁷ CD3⁺ cells/kg recipient weight, about 4×10⁷ CD3⁺ cells/kg recipient weight, about 1×10⁸ CD3⁺ cells/kg recipient weight, about 2×10⁸ CD3⁺ cells/kg recipient weight, about 4×10⁵ CD3⁺ cells/kg recipient weight, or about 5×10⁸ CD3⁺ cells/kg recipient weight.

Other concentrations are exemplified in U.S. Pat. Nos. 9,504,717; and 9,561,253, the contents of each of which are incorporated by reference herein in its entirety. The cellular product may contain CD34⁺ cells at a designated level of purity. For example, the cellular product may contain CD34⁺ cells that are at least 30%, at least 40%, at least 50%, at least 60%, at least 70%, at least 80%, at least 90%, at least 95%, at least 98%, or at least 99% pure. Other purities are exemplified in U.S. Pat. Nos. 9,504,717 and 9,561,253, the contents of each of which are incorporated by reference herein in its entirety.

The CD34⁺ cells and CD3⁺ cells may be provided as a mixture in one or more containers. The CD34⁺ cells and CD3⁺ cells may be provided in separate containers. Any commercially available container approved to hold cellar products may be used.

The cellular product may be provided frozen. Consequently, the cellular product may contain a cryoprotectant. Any cryoprotectant known in the art may be used. For example and without limitation, the cryoprotectant may be DMSO, dextran having an average molecular weight of 40 kDa, serum, e.g., bovine serum, albumin, e.g., human serum albumin, or cell culture medium. The cryoprotectant may be present at a defined concentration. For example, the cellular product may contain about 1% DMSO, about 2% DMSO, about 5% DMSO, about 7.5% DMSO, about 10% DMSO, about 12.5% DMSO, about 15% DMSO, or about 20% DMSO. The cellular product may contain about 1% dextran, about 2% dextran, about 5% dextran, about 7.5% dextran, about 10% dextran, about 12.5% dextran, about 15% dextran, or about 20% dextran. The cryoprotectant may be a commercially available freezing medium, such as the medium sold under the trade name CryoStor 10 by BioLife Solutions (Bothell, Wash.). Cryoprotection is discussed in U.S. Pat. Nos. 9,504,717 and 9,561,253, the contents of each of which are incorporated by reference herein in its entirety.

The cellular product may contain agents that enhance engraftment or functional mobilization of the hematopoietic cells in the recipient. The cellular product may contain agents that prevent a negative reaction of the recipient to the hematopoietic cells. For example and without limitation, the pharmaceutical composition may contain a cytokine, chemokine, growth factor, enzyme, substrate, excipient, carrier, antibody or a fragment thereof, small molecule, drug, agonist, antagonist, matrix protein, or complementary cell type.

In certain embodiments, the cellular product contains an enzyme, substrate, or both. For example, the cellular products may contain one or more alpha 1,3-fucosyltransferases, a fucose donor, or both. Fucosylation of HSPCs enhances binding to E-selectin and P-selectin and improves their ability to home to bone marrow. Examples of alpha 1,3-fucosyltransferase include alpha 1,3-fucosyltransferase IV, alpha 1,3-fucosyltransferase VI, and alpha 1,3 fucosyltransferase VII. The fucose donor may be GDP-fucose. Fucosylation of HSPCs is described in detail in U.S. Pat. No. 7,776,591, the contents of which are incorporated herein by reference.

The cellular product may contain a buffer. The cellular product may be buffer to maintain physiologically compatible pH. For example, the cellular product may be buffered to a neutral pH, such as from about 6.0 to about 8.0.

The cellular product may be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, see Cell Therapy: Stem Cell Transplantation, Gene Therapy, and Cellular Immunotherapy, by G. Morstyn & W. Sheridan. eds., Cambridge University Press, 1996; and Hematopoietic Stem Cell Therapy, E. D. Ball, J. Lister & P. Law, Churchill Livingstone, 2000.

The CD34⁺ cells, CD3⁺ cells, or both may be HLA-matched or HLA-mismatched to the recipient. Human leukocyte antigens (HLAs), also called major histocompatibility complex (MHC) antigens, are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells.

A key aspect of the HLA gene system is its polymorphism. Each gene exists in different alleles. Allelic gene products differ in one or more amino acids in the alpha and/or beta domain(s). An individual has two alleles of each gene, for a total of twelve alleles among the HLA-A, HLA-B, HLA-C, HLA-DP, HLA-DQ, and HLA-DR genes. An HLA-matched donor may have a match with the recipient at six, eight, ten, or twelve alleles selected from any combination of the HLA-A, HLA-B, HLA-C, HLA-DP, HLA-DQ, and HLA-DR genes. The genes most important for HLA typing are HLA-A, HLA-B, and HLA-DR, so the donor and recipient may be matched at all six alleles of the HLA-A, HLA-B, and HLA-DR genes. An HLA-mismatched donor may have a mismatch at one, two, three, four, five, six, or more alleles among the HLA-A, HLA-B, HLA-C, HLA-DP, HLA-DQ, and HLA-DR genes. HLA typing may be performed by any method known in the art. Examples of HLA typing methods include serological cytotoxicity, flow cytometry, and DNA typing. Such methods are described in, for example, U.S. Pat. No. 9,561,253, the contents of which are incorporated herein by reference.

The HLA genes are clustered in a super-locus present on chromosome position 6p21. Consequently, the set of alleles present on a single chromosome, i.e., a haplotype, tends to be inherited as a group. Identifying a patient's haplotypes can help predict the probability of finding matching donors and assist in developing a search strategy. Haplotypes vary in how common they are among the general population and in their frequency within different racial and ethnic groups.

Manufacture of cellular products from deceased donors may include additional characterization of the products. For example, a profile of one or more secreted molecules, such as cytokines or chemokines, may be established for compositions containing CD34$^+$ cells and/or CD3$^+$ cells. Alternatively or additionally, a profile of expression of cell surface markers, such as CD3, CD34, or CD45, may be established for the composition. Any suitable method may be used to characterize the compositions, including one or more of the methods described below in relation to analysis of blood from deceased donors. Cellular products may also be tested for the presence of pathogens, such as mycoplasma, or endotoxins that evidence the presence of pathogens.

Preparation of Cellular Products from Deceased Donors for Transfer to Living Recipients The invention provides methods of preparing cellular products that contain of CD34$^+$ cells and CD3$^+$ cells obtained from deceased donors. Given the predominant anatomical locations of CD34$^+$ cells and CD3$^+$ cells, as indicated above, different tissues or fluids are preferred sources for the two cell types. Therefore, the invention provides methods of obtaining CD34$^+$ cells from bone marrow of a deceased donor and obtaining CD3$^+$ cells from a different source, such as blood, liver, lymph nodes, spleen, or thymus, from the donor.

Bones include a hard outer layer, called cortical bone or compact bone, and an internal spongy portion, called cancellous bone, which contains the bone marrow. Bone marrow may be obtained from the cancellous bone material of large bones, such as the pelvis, vertebrae, ribs, femur, tibia, and sternum. Preferred sources of bone marrow are the iliac crests of the pelvis and vertebral bodies of the vertebrae.

The methods may include removal of bone marrow and a source of CD3$^+$ cells, such as blood, from the body of the deceased donor in either order. Preferably, the blood is removed first, i.e., the body is exsanguinated, and then the bone marrow is obtained. The methods may include removal of the solid organ of interest, such as a kidney, lung, pancreas, pancreatic islet cells, heart, intestine, colon, liver, skin, muscle, gum, eye, or tooth. The solid organ of interest, bone marrow, and source of CD3$^+$ cells, such as blood, may be removed in any order. Preferably, removal occurs in the following sequence: solid organ of interest, blood, and bone marrow.

Bone marrow may be removed from the body of the deceased donor by any suitable method. In some methods, bone marrow is removed by aspiration. Aspiration involves inserting a needle into the bone and withdrawing the bone marrow. In some methods, bone marrow is removed by trephination. A trephine is a saw with a circular blade that cuts into the bone to extract a cylindrical portion of bone.

FIG. 1 is an illustration of an external cortical cutting trocar 101 of a marrow extracting device according to an embodiment of the invention. The external trocar 101 includes a hollow shaft 113, which may be made of surgical steel. At the distal end of the external trocar 101 is a cutting tip 115, such as a toothed saw. The cutting tip 115 may be driven manually, pneumatically, or electrically. The cutting tip 115 and may be replaceable. At a proximal end of the external trocar 101 is a removable pneumatic drive adapter 117. The pneumatic drive adapter 117 couples the external trocar 101 with a pneumatic drive and may be removable from the external trocar 101. The external trocar 101 may include a suction adapter that couples the external trocar 101 to a vacuum pump or other suction source to facilitate removal of bone fragments. The suction adaptor may be fitted to the proximal end of the external trocar 101 when the drive adapter 117 is removed, or it may fit directly into the drive adapter 117.

Figure 2:
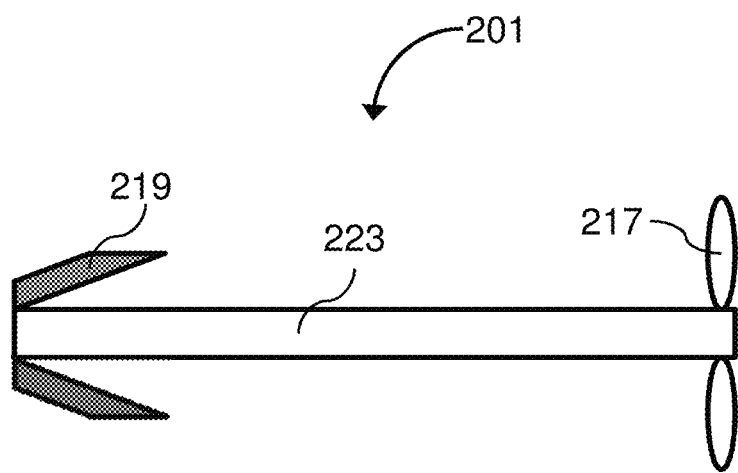
FIG. 2 is an illustration of the internal trocar of a marrow extracting device according to an embodiment of the invention.

FIG. 2 is an illustration of an internal trocar 201 of a marrow extracting device according to an embodiment of the invention. The internal trocar 201 includes a shaft 223 that has one or more deployable rongeur blades 219 positioned at the distal end. The rongeur blades can be positioned at different angles to achieve different circular cutting radii. Adjusting the cutting radius is useful for cutting into bones of different sizes. For example, a smaller cutting radius is needed for removal of vertebral bodies, whereas a larger cutting radius is optimal for extracting bone segments from the femur or tibia. The internal trocar 201 also includes one or more handles 217, or wings, at its proximal end. The handles 217 can be rotated by hand to allow manual extraction of bone segments. Alternatively or additionally, the internal trocar 201 may be coupled to a pneumatic drive for low-speed operation.

The following sequence of steps may be used to remove a portion of bone from a deceased donor. The following sequence is for illustrative purposes only, one of skill in the art will understand that other methods of bone removal are possible within the scope of the invention. First, a cortical surface of target bone is exposed by standard surgical procedure. Next, an external cutting trocar 101 with a cutting tip 115 and a pneumatic drive adapter 117 placed in the chuck of a pneumatic drive is used to cut through the cortex of the bone and into the medullary space. The pneumatic drive adapter 117 is then removed from the drive. Next, a solid internal trocar 201 is inserted through the shaft 113 of the external trocar 101, and the rongeur blades 219 are deployed. The handles 217 are used to twist the rongeur blades 219 and disrupt the medullary trabeculae. Alternatively, the internal trocar 201 can be engaged to a pneumatic drive at low speed. The internal trocar 201 is then removed from the shaft 113, and a suction adapter is affixed to the hollow trocar. Finally, a suction device is attached via the suction adapter, and suction is applied to evacuate the medullary space into a collection bag.

Because portions of bone obtained by trephination typically contain bone shards, methods of obtaining CD34$^+$ cells from portions of bone may include procedures to separate bone marrow cells from bone shards. A variety of methods may be use to isolate bone marrow cells from bone shards, such as physical agitation, enzymatic disaggregation, washing, and filtration. Methods may include treating the bone shards with one or more agents that mobilize hematopoietic cells, such as those agents described above, to improve the yield of HPSCs from the portions of bone. Treatment may include immersing bone shards in a preservation solution or liquid that contains one or more mobilizing agents. Treatment may occur within a storage container so that release of HSPCs occurs during the transport or shipping of extracted material. Thus, the portions of bone may be extracted from a donor at a first site and shipped to a recipient at a second site, and mobilization of hematopoietic cells may occur, at least in part, while the tissue is in transit.

HSPCs predominantly reside in the bone marrow as a result of molecular interactions with osteoblasts, stromal cells, and the extracellular matrix. In vivo, such interactions tether HSPCs to the bone marrow and prevent HSPCs from entering the circulating blood. During extraction of HSPCs, the same molecular interactions can hinder isolation of $CD34^+$ cells from other cell types and non-cellular material. Consequently, methods of preparing $CD34^+$ cells for use in cellular products to support organ transplantation may include treating bone marrow or a portion of bone with one or more agents that mobilize $CD34^+$ cells from bone marrow. Classes of agents that mobilize HSPCs from bone marrow include chemotherapeutics, hematopoietic growth factors, chemokines, inhibitors of chemokine receptors, and inhibitors of integrins. For example and without limitation, the mobilization agent may be an adenosine receptor antagonist, BIO5192, a CCR1 antagonist, a CCR2 antagonist, a CXCR2 antagonist, a CXCR4 antagonist, cyclophosphamide, defibrotide, EphA3-Fc, erythropoietin (EPO), glycosaminoglycan (GAG) mimetic, granulocyte colony stimulating factor (G-CSF), granulocyte macrophage colony stimulating factor (GM-CSF), growth-regulated oncogene beta (GRO-beta), human growth hormone, IL-8, macrophage inflammatory protein-1 alpha (MIP-1 alpha), met-SDF-1 beta, NSC23766, parathyroid hormone, pertussis toxin, plerixafor, a poly-[1-6]-D-glucopyranosyl-[1-3]-D-glucopyranose (PGG) glucan, a Rac1 inhibitor, a retinoic acid receptor agonist, SB290157, a SDF-1 alpha peptide analog, stem cell factor (SCF), sulfated colominic acid, a sulfated polysaccharide, T134, T140, thrombopoietin (TPO), a TPO receptor agonist, a VCAM-1 inhibitor a VLA-1 inhibitor, a VLA-4 inhibitor, or analog or derivative thereof.

Although bone marrow is the native environment for HSPCs, HSPCs represent only a small fraction of bone marrow cells. $CD34^+$ cells make up only about 1% of all nucleated cells in the bone marrow. Therefore, methods of the invention may include steps to enrich bone marrow extracts from deceased donors for $CD34^+$ cells.

One form of enrichment is to separate mononuclear cells from enucleated cells, such as red blood cells and platelets, and cells with multi-lobed nuclei, such as granulocytes, including neutrophils, basophils, and eosinophils. Several methods for enriching for isolating or enriching for mononuclear cells are known in the art. For example and without limitation, mononuclear cells may be isolated or enriched by buoyancy-activated cell separation, cell lysis, hetastarch sedimentation, immunomagnetic depletion, size-based centrifugal separation, and spinning membrane filtration. Systems for buoyancy-activated cell separation are commercially available from Cesca Therapeutics, Inc. (Rancho Cordova, Calif.) and described in, for example, U.S. Pat. No. 9,695,394, the contents of which are incorporated herein by reference. Systems for size-based centrifugal separation are commercially available from Sepax Technologies, Inc. (Newark, Del.). Systems for spinning membrane filtration are commercially available, such as the system sold under the trade name Lovo Automate Cell Processing System by Fresenius Kabi USA, LLC (Lake Zurich, Ill.).

$CD34^+$ cells may be purified based on qualitative or quantitative expression of one or more cell surface markers. Examples of suitable cell surface markers include AC133, CD3, CD34, CD38, CD45, and Thy-1. $CD34^+$ cells may be purified based on the presence or absence of a marker or on the level of expression of a marker, e.g., high vs. low. Purification of $CD34^+$ cells may include comparison of marker expression, complete blood cell counts, and/or mononuclear cell counts between starting material and material that has been enriched for $CD34^+$ cells.

$CD34^+$ cells may be purified by selectively binding a suitable affinity reagent to CD34 or another marker. The affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like. The affinity reagent may be directly conjugated to a detection reagent and/or purification reagent. The detection reagent and purification reagent may be the same, or they may be different. For example, the detection reagent and/or purification reagent may be fluorescent, magnetic, or the like. The detection reagent and/or purification reagent may be a magnetic particle for column purification. For example, magnetic column purification may be performed using the Miltenyi system of columns, antibodies, buffers, preparation materials and reagents, etc. known to those of skill in the art. Methods of affinity purification of hematopoietic cells, including $CD34^+$ and $CD3^+$ cells, and analysis of purified populations are described in, for example, U.S. Pat. Nos. 9,561,253; and 9,452,184, the contents of which are incorporated herein by reference.

$CD34^+$ cells may be isolated, enriched, or purified by any method. For example, $CD34^+$ cells may be isolated, enriched, or purified by column purification, flow cytometery, cell sorting, or immunoadsorption column separation. Preferably, $CD34^+$ cells are purified using an immunomagnetic column system, such as those sold under the trade name CliniMACS by Miltenyi Biotec Inc. (Auburn, Calif.), Methods of affinity purification of hematopoietic cells, including $CD34^+$ cells, and analysis of purified populations are described in, for example, U.S. Pat. Nos. 9,561,253; 9,452,184; Ng et al., Isolation of human and mouse hematopoietic stem cells, Methods Mol Biol. (2009) 506:13-21. doi: 10.1007/978-1-59745-409-4_2; and Spohn et al., Automated $CD34^+$ cell isolation of peripheral blood stem cell apheresis product, Cytotherapy (2015) October; 17(10): 1465-71. doi: 10.1016/j.jcyt.2015.04.005, the contents of each of which are incorporated herein by reference. The methods may include positive selection, negative selection, or both.

The methods may include various other treatments of bone marrow, blood, or other tissue sources that facilitate the recovery of $CD34^+$ cells and/or $CD3^+$ cells for use in the manufacture of product to administer to a living recipient. For example, blood, bone marrow, or other tissue may be treated to remove clots and/or cell clumps, i.e., agglutination. Clots and clumps may be removed by any suitable method. Non-limiting examples for removal of clots and clumps include filtration, e.g., spinning membrane filtration, as described above; treatment with thrombolytic drugs, such as alteplase, anistreplase, kabikinase, recombinant tissue plasminogen activators, reteplase, streptokinase, tenecteplase, and urokinase; ultrasound; and mechanical rubbing, as described in, for example, Khalil, et al., Rubbing Against Blood Clots Using Helical Robots: Modeling and In Vitro Experimental Validation, IEEE Robotics and Automation Letters (2(2):927-934, April 2017, DOI: 10.1109/LRA.2017.2654546, the contents of which are incorporated herein by reference.

Bone marrow, blood, or other tissue may be treated with one or more anticoagulants to prevent or minimize clotting. For example and without limitation, anticoagulants include acenocoumarol, antithrombin III, apixaban, argatroban, atromentin, betrixaban, bivalirudin, brodifacoum, dabigatran, dalteparin, difenacoum, edoxaban, EDTA, enoxaparin, fondaparinux, heparin, idraparinux, phenindione, phenprocoumon, rivaroxaban, and warfarin. The anticoagulant may be administered to the body of the deceased donor. Alternatively or additionally, the bone marrow, blood, or other tissue may be treated with the anticoagulant after removal from the body.

Bone marrow, blood, or other tissue may be treated to deplete red blood cells and/or platelets. For example and without limitation, red blood cells and/or platelets may be depleted by buoyancy-activated cell separation, cell lysis, hetastarch sedimentation, immunomagnetic depletion, size-based centrifugal separation, or spinning membrane filtration, as described above.

Methods for obtaining $CD3^+$ cells from blood may include separating blood into different constituents, such as a cellular fraction and a plasma fraction, as described in detail below.

Obtaining $CD3^+$ cells may include other methods of enriching blood or other non-bone marrouw sources for $CD3^+$ cells. Enrichment may include positive selection of $CD3^+$ cells, depletion of non-$CD3^+$ cells, or a combination thereof. For example and without limitation, $CD3^+$ cells may be positively selected by use of an antibody or other agent that binds a marker on the surface of $CD3^+$ cells, such as CD3, CD4, or CD8. For example and without limitation, depletion of non-$CD3^+$ cells may be depleted by use of an antibody agent that that binds a marker absent from the surface of $CD3^+$ cells, such as CD10, CD14, CD15, CD33, CD41, CD71, CD209, or CD235. Positive selection or depletion may be performed by binding antibodies conjugated to particles or beads to subpopulations of cells and sorting cell sub-populations by methods known in the art, such as those described in U.S. Pat. No. 9,090,871; U.S. Patent Publication No. 2010/0310588; and International Patent Publication No. WO 2017/005647, the contents of each of which are incorporated herein by reference.

During preparation of $CD34^+$ cells and/or $CD3^+$ cells for use in cellular products, cells may be frozen, i.e., cryopreserved, at any stage. Cryopreservation may include addition of one or more cryoprotectants, such as those described above in relation to cellular products of the invention. Cryopreservation typically involves reducing the temperature of the cell-containing sample at a controlled rate. Cryopreservation may include thawing the cell-containing sample and washing the sample to remove one or more cryoprotectants. Methods and reagents for cryopreservation, including freezing, thawing, and washing samples, are known in the art and described in, for example, U.S. Pat. No. 9,561,253, the contents of which are incorporated herein by reference.

In some circumstances, the number of $CD34^+$ cells and/or $CD3^+$ cells initially obtained from a deceased donor may be insufficient to generate a product to promote mixed chimerism in a living recipient. Therefore, the methods may include expanding $CD34^+$ cells and/or $CD3^+$ cells ex vivo. Any desired cell type or population of cells may be expanded. For example and without limitation, the population expanded may include HSPCs, T cells, T regulatory ($T_{reg}$) cells, memory T cells, effector memory T cells, central memory T cells, stem memory T cells, naïve T cells, cytotoxic T cells, gamma delta T cells, B cells, natural killer (NK) cells, natural killer T (NKT) cells, megakaryocytes, myeloblasts, monoblasts, monocytes, macrophages, dendritic cells, $CD34^+$ cells, $CD3^+$ cells, or $CD4^+$ cells Expansion may occur prior to, or subsequent to, freezing. Expansion may include providing one or more growth factors, and it may include culturing cells in the presence of another cell type, e.g., feeder cells. Methods for expanding hematopoietic cells are described in, for example, U.S. Pat. No. 9,561,253, the contents of which are incorporated herein by reference.

$CD34^+$ cells and/or $CD3^+$ cells may be genetically modified ex vivo. For example, in autologous transfer of donor cells, a genetic defect may be corrected using gene therapy. Methods of gene therapy are described in, for example, Mali, Delivery systems for gene therapy, Indian J Hum Genet. 2013 January-March; 19(1): 3-8, doi: 10.4103/0971-6866.112870; Gennady Ermak (2015) FRONT MATTER. Emerging Medical Technologies, ISBN: 978-981-4675-80-2, doi.org/10.1142/9789814675826_fmatter; and Bakhuraysah et al., Hematopoietic stem cell transplantation for multiple sclerosis: is it a clinical reality? Stem Cell Res Ther. 2016; 7:12, doi: 10.1186/s13287-015-0272-1, the contents of each of which are incorporated herein by reference.

Ex Vivo Extraction of Hematopoietic Cells from Bone Marrow

The invention also provides methods for extracting hematopoietic cells, such as $CD34^+$ cells, from the bone marrow of a deceased donor for use in manufacture of cellular products to transfer to a living recipient. As indicated above, $CD34^+$ cells in adults reside predominantly in the bone marrow, where they are tethered to other cells and to the extracellular matrix. $CD34^+$ cells can be mobilized to enter the blood in living patients by treatment with agents that disrupt the interactions between $CD34^+$ cells and components of the bone marrow, but maximal mobilization takes several days. The mobilization of $CD34^+$ cells in the body slows any manufacturing process and, in the case of deceased donors, prolongs exposure of the cells to cytokines and other factors released upon brain death. The invention provides methods that improve harvesting of $CD34^+$ cells from the bone marrow of deceased donors by performing mobilization ex vivo, which can speed the manufacturing process because extraction of $CD34^+$ cells can occur in a container while bone marrow is being shipped to a manufacturing facility.

Ex vivo extraction of hematopoietic cells from bone marrow expedites the production of cellular compositions of the invention. Extraction involves contacting a bone sample with one or more agents that facilitate release of cells of interest from the bone marrow, such as the agents that mobilize $CD34^+$ cells described above, while the bone sample is in a container. Thus, the step can be performed while the sample is in storage or being transported to a processing facility. In addition, because ex vivo extraction allows rapid recovery of bone marrow cells, it improves the quality of cells for use in manufacture of products to promote mixed chimerism.

The methods involve obtaining a bone sample from a deceased donor. The sample may be from any large bone that contains the cancellous material, such as the pelvis, vertebrae, ribs, femur, tibia, and sternum. Preferably, the sample is from the iliac crests of the pelvis and vertebral bodies of the vertebrae.

The methods further involve obtaining bone marrow cells from the bone sample after it has been removed from the body. Bone marrow cells may be obtained from the bone sample by any method. For example, bone marrow cells may be obtained by trephination or aspiration, as described above. Samples obtained by trephination may be treated to remove bone shards, as described above.

The methods may include treating the bone sample with an agent that mobilizes CD34$^+$ cells from bone marrow, such as one of the mobilizing agents described above.

The methods may be used to obtain any type of hematopoietic cells. For example and without limitation, the cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, CD34$^+$ cells, CD4$^+$ cells, or CD3$^+$ cells. Preferably, the cells are HSPCs or CD34$^+$ cells.

The methods may include one or more additional steps, such as those described above in relation to preparation of cellular products. For example, the methods may include any of the following: treating the hematopoietic cells with an anticoagulant, such as one described above; depleting the hematopoietic cells or red blood cells and/or platelets; and enriching the hematopoietic cells for a cell type or population of cells, such as CD34$^+$ cells.

The methods may include using the hematopoietic cells extracted from bone marrow ex vivo for use in manufacture of a product for transfer into a living recipient, such as one of the cellular compositions described above.

The invention also includes materials useful for ex vivo extraction of hematopoietic cells, such as CD34$^+$ cells, from bone marrow of deceased donors. For example, the invention provides receptacles that are pre-loaded with one or more agents that mobilize CD34$^+$ cells from bone marrow, such as one of the mobilizing agents described above. The invention also includes systems that include a container that contains one or more such agents and one or more portions of bone derived from a deceased donor.

The materials and systems for ex vivo extraction of hematopoietic cells may be characterized by their ability to release particular cell type or population of cells into suspension over time. For example, the materials and systems may increase the release of CD34$^+$ cells from bone marrow as compared to a reference storage system by 2-fold, 3-fold, 4-fold, 5-fold, 10-fold, 20-fold, 50-fold, 100-fold, 200-fold, 500-fold, 1000-fold, or more.

The materials and systems for ex vivo extraction of hematopoietic cells may achieve release of a particular cell type or population of cells into suspension in a defined period, such as 1 hour, 2 hours, 4 hours, 8 hours, 12 hours, 24 hours, 48 hours, 72 hours, 96 hours, or more.

The materials and systems may achieve release into suspension of a particular cell type or population of cells having characteristics that improve the utility of the cells for manufacture of products to promote mixed chimerism. For example and without limitation, the cells may have superior viability, proliferation potential, marker expression, apoptotic characteristics, and/or apoptotic characteristics as compared to cells from a reference storage system.

Fractionation of Blood from Deceased Donors

The invention also provides methods of fractionating blood from deceased donors into two or more constituents and using one or more of the constituents in the manufacture of products for transfer into living recipients. Apheresis of blood from live donors involves separation of blood into different constituents, isolating one or more constituents, and returning the remainder to circulation. For example, leukapheresis entails the isolation of white blood cells from the blood of a donor and returning the remaining cells and plasma to the donor's body. Apheresis methods and devices are known in the art and described in, for example, U.S. Publication No. 2002/0107469; U.S. Pat. Nos. 5,607,579; 9,364,600; and 6,743,192, the contents of each of which are incorporated herein by reference.

The invention provides methods in which procedures analogous to apheresis are used to separate components of blood from deceased donors. An advantage of using blood from deceased donors is that the unused portion of blood need not be returned to the donor's body after isolation of the component of interest. For example, blood from a deceased donor may be separated into a cellular fraction and a plasma fraction or into two or more different cellular fractions. The blood may be fractionated sequentially. For example, after initial separation into cellular and non-cellular fractions, the cellular fraction may be further processed to enrich for a particular cell type of population of cells, such as CD3$^+$ cells. Any method known in the art may be used to enrich for CD3$^+$ cells, including any of the methods described above.

Separating blood from a deceased donor into different fractions is useful for obtaining fractions that are enriched for particular components, such as cell types or populations of cells, to be included in cellular products of the invention. The cells may be any type of hematopoietic cells, such as B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, CD34$^+$ cells, CD4$^+$ cells, or CD3$^+$ cells. In particular, blood fractionation is useful for obtaining fractions enriched for CD3$^+$ cells for use in manufacture of cellular products. Fractionation of blood is also useful to obtain fractions enriched for CD34$^+$ cells, which can be used to supplement the bone marrow-derived CD34$^+$ cells in products of the invention.

Several insights of the invention allow the use of fractionated blood from deceased donors in the manufacture of cellular products for transfer into living recipients. One is that devices and methods of the invention for collection of blood from deceased donors, as described below, permit blood to be removed rapidly from the body, collected in one or more sterile receptacles, and refrigerated to a storage temperature that preserves activity of blood cells. The invention also enables the use of fractionated blood from deceased donors by providing methods of enriching for cell types of interest, such as CD34$^+$ cells and CD3$^+$ cells, as described above. Another advancement that makes fractionated blood from deceased donors useful for the manufacture of therapeutic products is the ability to characterize the fractionated products via analytical methods, described below, to determine their utility as starting material for such products.

The methods of fractionation methods may be performed on blood that has been supplemented with additional components from the deceased donor. For example, cells extracted from bone marrow or other tissues, as described above, may be combined with blood to enrich for a desired cell type of population of cells in the mixture. For example and without limitation, the population enriched may include HSPCs, T cells, T regulatory (T$_{reg}$) cells, memory T cells, effector memory T cells, central memory T cells, stem memory T cells, naïve T cells, cytotoxic T cells, gamma delta T cells, B cells, natural killer (NK) cells, natural killer T (NKT) cells, megakaryocytes, myeloblasts, monoblasts, monocytes, macrophages, dendritic cells, CD34$^+$ cells, CD3$^+$ cells, or CD4$^+$ cells The cells extracted from bone marrow or other tissue may have been subjected to any of the procedures described above to enrich for CD34$^+$ cells and CD3$^+$ cells. The supplemented blood may then be separated into fractions, as described above.

Analysis of Blood from Deceased Donors

The invention also provides analytical methods to determine whether blood from deceased donors to determine whether the blood is suitable for use in manufacture of a product to administer to a living recipient. The methods may involve analysis of the blood itself, or they may involve analysis of other tissue from the deceased donor. The analytical methods may be combined with any of the preparative methods described above.

The methods are useful for determining whether material in blood is suitable for use in manufacture of products for transfer to a living recipient. Preferably, the material from the blood is a cell type or population of cells. For example and without limitation, the cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory (T$_{reg}$) cells, memory T cells, effector memory T cells, central memory T cells, stem memory T cells, naïve T cells, cytotoxic T cells, gamma delta T cells, natural killer T cells, CD34$^+$ cells, CD4$^+$ cells, or CD3$^+$ cells. The analytical methods may be combined with any of the preparative methods described above. Alternatively or additionally, the material from the blood may be a non-cellular component, such as a molecule. For example and without limitation, the molecule may be a cytokine, chemokine, antibody, or immunoglobulin.

Analysis of several characteristics of T cells from deceased donors is useful for determining whether T cells will promote mixed chimerism in a transplant recipient. For example and without limitation, analyses of T cell activation, anergy, apoptosis, exhaustion, proliferation, viability, and cytokine secretion provide information that may be used to assess whether the T cells may provide a therapeutic benefit to a living recipient.

Characterization of T cells or CD3$^+$ cells from a deceased donor may include analysis of cells in the blood. Any suitable assay may be used. For example and without limitation, the methods may include proliferation assays, DNA synthesis assay, apoptosis assays, colony formation assays, marker expression assays, and the like. Methods of analysis of T cells are known in the art and described in, for example, Brousseau, et al., eds., Manual of Immunological Methods, CRC Press, Boca Raton, 1998, ISBN 9780849385582; Detrick, et al., eds., Manual of Molecular and Clinical Laboratory Immunology, Eighth Edition, American Society for Microbiology Press, Washington D.C., USA, 2016, ISBN-13: 978-1555818715; and Balakrishnan, et al., Practical Immunology: A Laboratory Manual, Lap Lambert Academic Publishing, 2017, ISBN-13: 978-3330352032, the contents of each of which are incorporated herein by reference.

Characterization of T cells or CD3$^+$ cells from a deceased donor may include analysis of a non-cellular component of the blood. For example and without limitation, the non-cellular component may be a cytokine, e.g., a pro-inflammatory or anti-inflammatory cytokine, a chemokine, an antibody, or an immunoglobulin. Non-cellular components may be analyzed in serum or plasma from the deceased donor. Non-cellular components may be analyzed by immunoassays, such as an enzyme-linked immunoassay (ELISA), radioimmunoassay, immunoPCR, and immunoassay systems sold under the trade names Luminex xMAP by ThermoFisher Scientific (Waltham, Mass.); Meso Scale Discovery by Meso Scale Diagnostics (Rockville, Md.); AlphaLISA and DELFIA by Perkin Elmer (Waltham, Mass.); Gyrolab by Gyros Protein Technologies (Uppsala, Sweden); and Erenna by MilliporeSigma (Burlington, Mass.). Other methods of analysis of non-cellular components are known in the art and described in, for example, Brousseau, et al., eds., Manual of Immunological Methods, CRC Press, Boca Raton, 1998, ISBN 9780849385582; Detrick, et al., eds., Manual of Molecular and Clinical Laboratory Immunology, Eighth Edition, American Society for Microbiology Press, Washington D.C., USA, 2016, ISBN-13: 978-1555818715; and Balakrishnan, et al., Practical Immunology: A Laboratory Manual, Lap Lambert Academic Publishing, 2017, ISBN-13: 978-3330352032, the contents of each of which are incorporated herein by reference.

The methods may include analysis of whether HSPCs or CD34$^+$ cells in the blood from a deceased donor are suitable for use in manufacture of products for transfer into living recipients. Properties such as HSPC proliferation, HSPC viability, and HSPC apoptosis may be analyzed to determine whether HSPCs in the blood may provide a therapeutic benefit may be used to assess whether HSPCs may provide a therapeutic benefit to a living recipient. For example and without limitation, analysis may include colony-forming assays or long-term culture assays that measure cell growth in response to exogenous growth factors. Analysis may include assays for the ability of HSPCs to repopulate themselves in a mouse model, such as a severe-combined immunodeficiency (SCID) mouse. These and other methods are known in the art and described in, for example, Loring and Peterson, eds., Human Stem Cell Manual: A Laboratory Guide, Second Edition, Academic Press, 2012, ISBN: 978-0-12-385473-5; Stein, et al., eds., Human Stem Cell Technology and Biology: A Research Guide and Laboratory Manual, Wiley-Blackwell, 2011, ISBN 978-0-470-59545-9; Frisch and Calvi, Hematopoietic Stem Cell Cultures and Assays, Methods Mol Biol. 2014; 1130: 315-324, doi: 10.1007/978-1-62703-989-5_24; Dick J E, et al., Assay of human stem cells by repopulation of NOD/SCID mice, Stem Cells, 1997; 15 Suppl 1:199-203; discussion 204-7, DOI: 10.1002/stem.5530150826; and T Tatekawa, et. al., (2006) A novel direct competitive repopulation assay for human hematopoietic stem cells using NOD/SCID mice, Cytotherapy, 8:4, 390-398, DOI: 10.1080/14653240600847191, the contents of each of which are incorporated herein by reference.

The analysis may include providing a report of the characteristics of the blood or non-blood tissue from the deceased donor. For example and without limitation, the report may include percentages of cells that have any of the following properties: expression of a marker, viability, proliferation potential, apoptotic characteristics, anergy, exhaustion, activation, and cytokine secretion. The report may describe characteristics of sub-populations of cells. For example and without limitation, the report may include percentages of viability, proliferation potential, apoptotic characteristics, anergy, exhaustion, activation, or cytokine secretion of cells that express a particular marker, such as $CD34^+$ cells, or $CD3^+$ cells.

Determination of whether material in the blood is suitable for use in manufacture of product for transfer into living recipients may include analysis of non-blood tissue from the deceased donor. For example and without limitation, the non-blood tissue may be bone marrow, spleen, liver, lymph nodes, or thymus. Cellular components, e.g., hematopoietic cells, such as those described above, or non-cellular components, such as the molecules described above, of non-blood tissue may be analyzed. Any analytical methods, including those described above may be used.

The content and location of hematopoietic cells in the body vary during growth and development. For example, the spleen is a rich source of lymphocytes in adults, whereas the liver contains many lymphocytes in the developing fetus. Therefore, the tissue source of hematopoietic cells may account for the age of the donor at the time of death.

The methods may include analysis of multiple components. The multiple components may come from the same source, or they may come from different sources. For example, the methods may include analysis of multiple cellular components of the blood, multiple non-cellular components of the blood, multiple components of a non-blood tissue, or any combination of a cellular blood component, a non-cellular blood component, and a component of non-blood tissue.

To better determine whether components from the blood of a deceased donor are suitable for use in manufacture of products for transfer to a living recipient, analysis may include comparison of one or more parameters from a tissue or fluid of a deceased donor to the corresponding material from a living donor. Analysis may include a comparison of any characteristic described above. For example and without limitation, analysis may include comparison of one or more of T cell activation, T cell anergy, T cell apoptosis, T cell exhaustion, T cell proliferation, T cell viability, T cell cytokine secretion, HSPC proliferation, HSPC viability, HSPC apoptosis, cytokine levels, chemokine levels, antibody levels, and immunoglobulin levels.

The determination of whether blood or a blood component from a deceased donor is suitable for use in manufacture of products for transfer to a living recipient may rely on a comparison of one or more parameters between the deceased donor and a living donor. For example, when the value of one more parameters from a deceased donor is comparable to the corresponding values from a living donor or population of living donors, the blood or blood component from a deceased donor may be deemed suitable for use in manufacture of products for transfer to a living recipient. Comparative analysis may include establishing a profile of characteristics for living donors and for donors at various temporal stages following brain death.

Values may be compared between a deceased donor and living donor or population of living donors that meet one or more criteria. For example, the living donor or population of living donors may have done of the following: previously donated a solid organ; previously donated hematopoietic cells, such as HSPCs or T cells; or previously donated tissue that supported establishment of mixed chimerism in a recipient. The living donor or population of living donors may be healthy, within a particular age range, of a certain sex, or the like.

The methods may include using one or materials from the blood of a deceased donor in the manufacture of a product for transfer to a living recipient. The materials may be any materials described above, such as cellular or non-cellular components.

The methods may include expansion of a cell type or population of cells for use in the manufacture of a product for transfer to a living recipient. For example, the cells may be B cells, basophils, eosinophils, hematopoietic cells, hematopoietic stem and progenitor cells (HSPCs), lymphocytes, lymphoid progenitor cells, macrophages, mast cells, megakaryocytes, monocytes, myeloblasts, myeloid progenitor cells, natural killer (NK) cells, neutrophils, platelets/thrombocytes, T cells, T regulatory ($T_{reg}$) cells, memory T cells, effector memory T cells, central memory T cells, stem memory T cells, naïve T cells, cytotoxic T cells, gamma delta T cells, natural killer T cells, $CD34^+$ cells, $CD4^+$ cells, or $CD3^+$ cells.

The methods may include treating blood from a deceased donor to mitigate damage to material in the blood that may be used in manufacture of a product for transfer into living recipients. For example, the methods may include adding an anticoagulant, buffer, cryoprotectant, or stabilizer to the blood. The stabilizer may prevent degradation of blood component or may promote osmotic stability. For example, the stabilizer may be human serum albumin (HSA) or the electrolyte solution sold under the trade name Plasma-Lyte by Baxter International Inc. (Deerfield, Ill.).

The methods may include cryopreserving the products. The products may be frozen at a temperature suitable for long-term storage, such as about −150° C. The methods may include gradually reducing the temperature of the product to the long-term storage temperature.

Devices and Methods for Collection of Blood from Deceased Donors

The invention also provides device and methods for collection of blood from a deceased donor for use in manufacture of products for transfer to a living recipient. Blood must be expeditiously processed for use as a source of material for transfer into a living recipient. In particular, it must be removed from the body rapidly after brain death, preferably within hours, before the release of cytokines that can alter the function of blood cells. In addition, blood must be rapidly chilled to a suitable short-term storage temperature, typically 2-8° C., upon removal from the body, but freezing should be avoided until the blood or blood products are ready for cryopreservation. Given that the total blood volume of an adult human may be 5 liters or more and that maximal recovery is needed to obtain sufficient quantities of $CD34^+$ and $CD3^+$ cells, collection of blood from deceased donors presents unique challenges.

Figure 3:
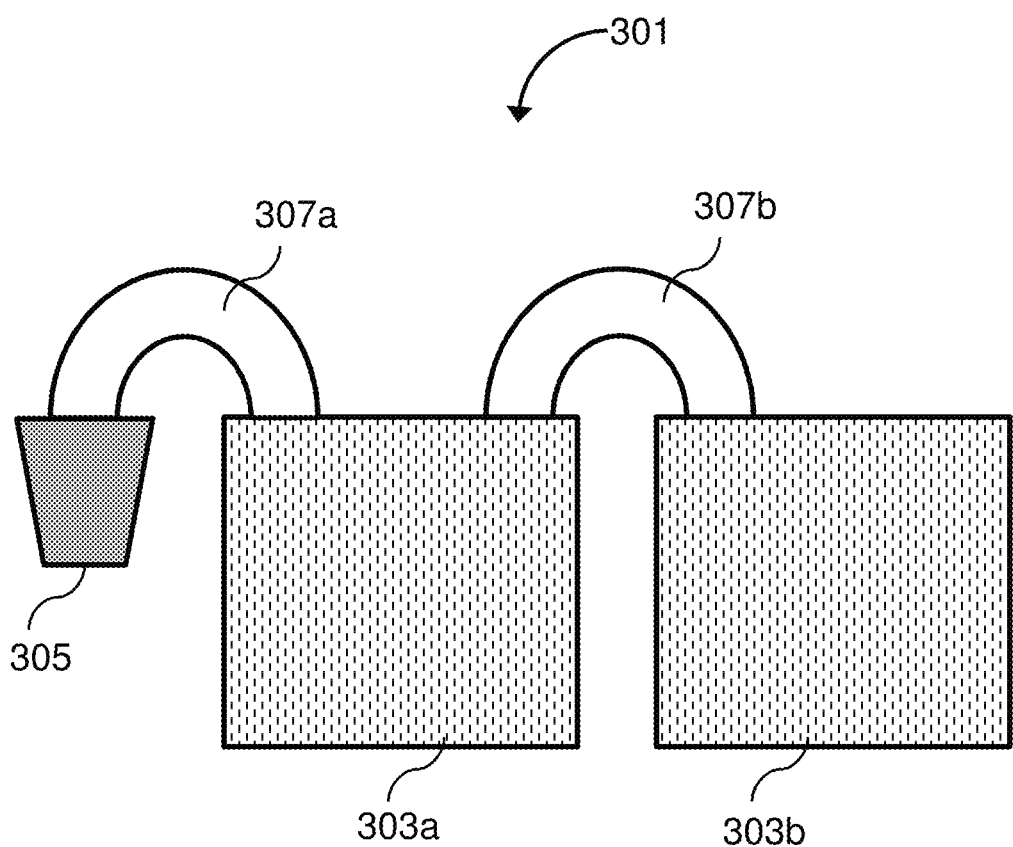
FIG. 3 shows a blood collection device according to an embodiment of the invention.

FIG. 3 shows a blood collection device 301 according to an embodiment of the invention. The device 301 includes one or more receptacles 303a and 303b coupled to a cooling system. The receptacles may have a combined capacity of about 0.5, 1, 2, 3, 4, 5, 6, 7, 8, 9, or 10 liters, and preferably from about 5 to about 10 liters. The devices may have 1, 2, 3, 4, 5, 6, 7, 8, 9, 10, or more receptacles. The receptacles may be rigid and have a fixed shape, or they may be flexible and expandable. For example and without limitation, the receptacles may be cups, bottles, cylinders, bags, pouches, or the like. The receptacles may be made from a flexible or pliable plastic. In an embodiment, each receptacle is a rectangular prism of 25 cm×20 cm×2 cm and has a capacity of 1 liter.

The device 301 may include one or more cannulae 305 that can be inserted into a vein or artery of the deceased donor. The cannula may be connected to one or more receptacles 303a and 303b by a connector 307a, such as tubing. In a device 301 having multiple receptacles 303a and 303b, blood may be collected into the receptacles 303a and 303b in parallel, sequentially, or some combination thereof. In devices that have receptacles arranged in sequence, the receptacles 303a and 303b may be joined by connectors 307b. One or more of the connectors 307a and 307b may include a one-way valve to prevent reverse flow of blood through the device 301, thereby minimizing contamination of the blood and maintaining its sterility.

Figure 4:
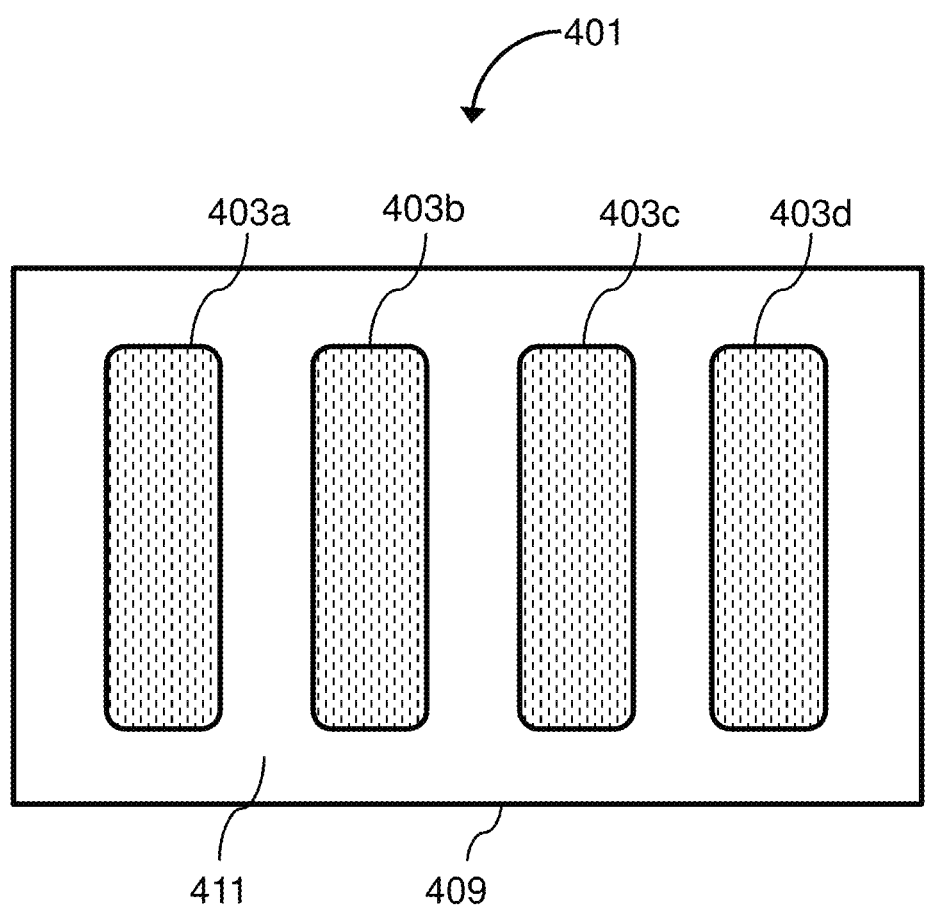
FIG. 4 shows a blood collection device according to an embodiment of the invention.

FIG. 4 shows a blood collection device 401 according to an embodiment of the invention. The device includes receptacle 403a, 403b, 403c, and 403d disposed within a refrigeration compartment 409. The refrigeration compartment 409 includes a coolant 411 that cools blood after its removal from the donor. Any suitable coolant 411 may be used. For example and without limitation, the coolant 411 may include ammonium chloride, ammonium nitrate, brine, calcium ammonium nitrate, diethylene glycol, hydroxyethyl cellulose, ice, propylene glycol silica gel, sodium polyacrylate, urea, or water.

The cooling system is configured to cool blood in the receptacles to a target temperature. The target temperature may from about 2° C. to about 8° C. The cooling system may prevent blood from freezing or formation of ice crystals within the blood. The cooling system may cool blood to the target temperature within a specified period. For example, the cooling system may cool blood to the target temperature in about 4 hours, about 5 hours, about 6 hours, about 7 hours, about 8 hours, about 9 hours, about 10 hours, not less than 4 hours, not less than 5 hours, not less than 6 hours, not less than 7 hours, not less than 8 hours, not more than 6 hours, not more than 7 hours, not more than 8 hours, not more than 9 hours, or not more than 10 hours. The device may include a vacuum system configured to apply a vacuum to remove blood from the deceased donor. The vacuum system may be a pump. Vacuum pumps for blood collection are known in the art and described in, for example, U.S. Patent Publication No. 2010/0042015; and U.S. Patent Publication No. 2008/0199949, the contents of each of which are incorporated herein by reference. The vacuum system may be coupled to one or more of the needle, tubing, and receptacle.

The invention provides methods for removal of blood from a deceased donor using devices of the invention. The methods include transferring blood to one or more receptacles coupled to a cooling system. The methods may include inserting a needle into a blood vessel, artery, or vein of the deceased donor. The methods may include applying a vacuum to the blood vessel, artery, or vein of the deceased donor. The methods may include contacting the blood with a stabilizing agent or cryoprotectant, such as one described above.

Treating Organ Transplant Recipients Using Cellular Products Derived from Deceased Donors The cellular products of the invention may be provided to the recipient of a solid organ transplant. The cellular product may be provided by any suitable means. For example and without limitation, the CD34$^+$ cells and/or CD3$^+$ cells may be delivered to the recipient by injection using a needle, catheter, central line, or the like. In some cases, the cells may be delivered intravascularly, intravenously, intraarterially, subcutaneously, intramuscularly, directly to the bone, or through any source which permits the hematopoietic cells to home to an appropriate site in the recipient such that the hematopoietic cells persist, regenerate and differentiate in the recipient. The CD34$^+$ cells and/or CD3$^+$ cells may be provided by infusion. The CD34$^+$ cells and/or CD3$^+$ cells may be provided in an inpatient procedure or in an outpatient procedure. An inpatient procedure requires admission to a hospital, and the patient may spend one or more nights in the hospital. An outpatient procedure does not require admission to a hospital and may be performed in a non-hospital setting, such as a clinic, doctor's office, home, or other location.

The compositions of the invention may be used in conjunction with transplantation of any solid organ. For example and without limitation, the solid organ may be a kidney, lung, pancreas, pancreatic, islet cells, heart, intestine, colon, liver, skin, muscle, gum, eye, or tooth. The transplant may include a complete organ, a portion of an organ, or cells from a tissue of an organ. The cellular product may be provided prior to, during, or subsequent to the solid organ transplant. For example and without limitation, the cellular product may be provided one, two, three, four, five, or six days or one, two, three, or four weeks prior to the solid organ transplant, or it may be provided one, two, three, four, five, or six days or one, two, three, or four weeks after the solid organ transplant.

To facilitate establishment of mixed chimerism in the recipient, the recipient's immune system may be conditioned in conjunction with providing the cellular product. For example, non-myeloablative conditioning may be used. In non-myeloablative conditioning, the recipient is exposed to drugs, antibodies, irradiation, or some combination thereof at a dose that is too low to eradicate all the bone marrow cells. Typically, the conditioning regimen includes treatment with anti-thymocyte globulin (ATG), total lymphoid irradiation, and corticosteroids (e.g. prednisone) for a period of from about 10 to 12 days (e.g. for about 11 days). The irradiation may be targeted to a particular location of the recipient's body. For example, irradiation may be targeted to a tissue, an organ, a region of the body or the whole body. Irradiation may be targeted to the lymph nodes, the spleen, or the thymus or any other area known to a person of skill in the art. When multiple doses of irradiation are administered, the doses may be targeted to the same location or to different locations. Non-myeloablative conditioning may include the use of a T cell depleting agent, such as a monoclonal antibody or drug, e.g., fludarabine. Regimens for non-myeloablative conditioning are known in the art and are described in, for example, U.S. Pat. No. 9,561,253, the contents of which are incorporated herein by reference.

The methods may include immunosuppressive therapy. Immunosuppressive therapy, or immunosuppression, involves treatment of the graft recipient with agents that diminish the response of the host immune system against the donor cells, which can lead to graft rejection. Primary immunosuppressive agents include calcineurin inhibitors, such as tacrolimus, cyclosporin A. Adjuvant agents are usually combined with a calcineurin inhibitor. Adjuvant agents include steroids, azathioprine, mycophenolic acid (MPA) agents, such as mycophenolate mofetil, mTOR inhibitors, such as sirolimus, and belatacept. The use of adjuvant agents allows clinicians to achieve adequate immunosuppression while decreasing the dose and toxicity of individual agents. Antibody-based therapy may use monoclonal (e.g., muromonab-CD3) or polyclonal antibodies or anti-CD25 antibodies (e.g., basiliximab, daclizumab). Antibody-based therapy allows for avoidance or dose reduction of calcineurin inhibitors, possibly reducing the risk of nephrotoxicity. Regimens for immunosuppressive therapy are known in the art and are described in, for example, U.S. Pat. No. 9,561,253, the contents of which are incorporated herein by reference.

Immunosuppression may also diminish the response of the donor immune cells against recipient tissue, which can lead to GVHD. GVHD may be acute or chronic. Acute GVHD typically occurs in the first 3 months after graft and may involve the skin, intestine, or the liver. Treatment for acute GVHD usually includes high-dose corticosteroids such as prednisone. Chronic GVHD typically occurs after the first 3 months following transplant and is the major source of late treatment-related complications. Chronic GVHD may cause functional disability and require prolonged immunosuppressive therapy.

Immunosuppressive therapy may occur in multiple phases. For example, the immunosuppressive regimen may have an induction phase and a maintenance phase. Induction and maintenance phase strategies may use different medicines at doses adjusted to achieve target therapeutic levels to enhance establishment of mixed chimerism in the recipient.

Immunosuppressive therapy may be withdrawn after stable mixed chimerism has been established in the recipient. The chimeric status of the recipient may be monitored as described below and deemed stable after a certain period, for example, 3 months, 6 months 12 months, 18 months, 24 months, or longer. Thus, immunosuppression may be discontinued for the recipients after a certain period, for example, 3 months, 6 months 12 months, 18 months, 24 months, or longer. Withdrawal of immunosuppressive therapy may include tapering, i.e., progressively reducing the dosage or frequency of treatment.

A determination of whether an individual is a full chimera, mixed chimera, or non-chimera made be made by an analysis of a hematopoietic cell sample from the solid organ transplant recipient, e.g. peripheral blood, bone marrow, etc. as known in the art. Analysis may be done by any convenient method of typing. Analysis may be performed on hematopoietic cells or a subset thereof, such as all mononuclear cells, T cells, B cells, $CD56^+$ NK cells, and $CD15^+$ neutrophils. Chimerism can be assessed by PCR analysis of microsatellites. For example, commercial kits that distinguish polymorphisms in short terminal repeat lengths of donor and host origin are available. Automated readers provide the percentage of donor type cells based on standard curves from artificial donor and host cell mixtures.

Recipients may be categorized as fully chimeric, mixed chimeric, or non-chimeric based on the fraction of cells that are derived from the donor. For example, recipients can be deemed fully chimeric if they have at least 90%, at least 95%, at least 98%, or at least 99% donor-derived cells. Recipients can be deemed mixed chimeric if they have too few donor-derived cells to be categorized as fully chimeric but a fraction of donor-derived cells that exceeds a certain threshold, such as at least 0.5%, at least 1%, at least 2%, at least 3%, at least 5%, at least 7.5%, at least 10% donor-derived cells. Recipients can be deem non-chimeric if the fraction of donor-derived cells falls below the threshold required to be categorized as mixed chimeric.

Cellular Products Derived from a Single Deceased Donor for Transfer to Multiple Living Recipients The invention also provides multiple cellular products derived from a single deceased donor for transfer to multiple living recipients. The generation of multiple cellular products containing $CD34^+$ cells and $CD3^+$ cells from a single donor allows the products to be transferred to different recipients. Thus, two or more solid organs from the deceased donor may be transplanted into different recipients, and each recipient may also receive donor $CD34^+$ and $CD3^+$ cells that promote establishment mixed chimerism. For example, the products and methods of the invention allow a single deceased donor to provide a kidney and product containing $CD34^+$ cells and $CD3^+$ cells to each of two recipients. Consequently, the products and methods of the invention increase the number of patients who can benefit from organ transplantation procedures without requiring additional organ donors.

A single deceased donor may be the source of material for 1, 2, 3, 4, 5, or more cellular products that promote mixed chimerism in a solid organ transplant recipient. The multiple cellular products from a single deceased donor may comprise any element of the cellular products described above, such as cell type, cell number, degree of HLA matching or mismatching, cell purity, cryoprotectants, stabilizing agents, or graft-enhancement agents.

The invention also provides methods of preparing multiple cellular products from a single deceased donor for transfer to multiple living recipients. The methods include obtaining $CD34^+$ cells from bone marrow of a deceased donor and $CD3^+$ cells from non-bone marrow of the donor. The methods may include any element described above in relation to preparation of cellular products, ex vivo extraction of $CD3^+$ cells from non-bone marrow, fractionation of blood, or analysis of blood. For example and without limitation, the methods may include one or more of removal of bone marrow, separation of cells from bone shards, treatment with an agent that mobilizes $CD34^+$ cells, separation of mononuclear cells from enucleated or multinucleated cells, depletion of RBCs and platelets, enrichment of $CD34^+$ cells and/or $CD3^+$ cells, removal of clots and/or cell clumps, treatment with an anticoagulant, cryopreservation, ex vivo expansion of cells, genetic modification of cells, and analysis of T cell activation, T cell anergy, T cell apoptosis, T cell exhaustion, T cell proliferation, T cell viability, T cell cytokine secretion, HSPC proliferation, HSPC viability, HSPC apoptosis, cytokine levels, chemokine levels, antibody levels, and/or immunoglobulin levels.

EXAMPLES

Example 1

A method of preparing a cellular composition containing $CD34^+$ cells derived from bone marrow of a deceased donor and $CD3^+$ cells derived from blood of the deceased donor according to an embodiment of the invention is described below.

FIG. 1 is a flow diagram illustrating a method of preparing a cellular composition containing $CD34^+$ cells derived from bone marrow of a deceased donor and $CD3^+$ cells derived from blood of the deceased donor according to an embodiment of the invention. The method includes a series of steps, which are described in more detail below. The method includes the following steps: collection of tissue; preparation of bone marrow; preparation of blood; preparation of buffer; enrichment of $CD34^+$ cells from bone marrow; dividing the combined material into individual doses; and cryopreservation. The sequence of steps described herein is for illustrative purposes only. Although it will be understood by one of skill in the art that certain steps must be performed prior to others, the methods are not limited to a particular sequence of steps.

Figure 5:
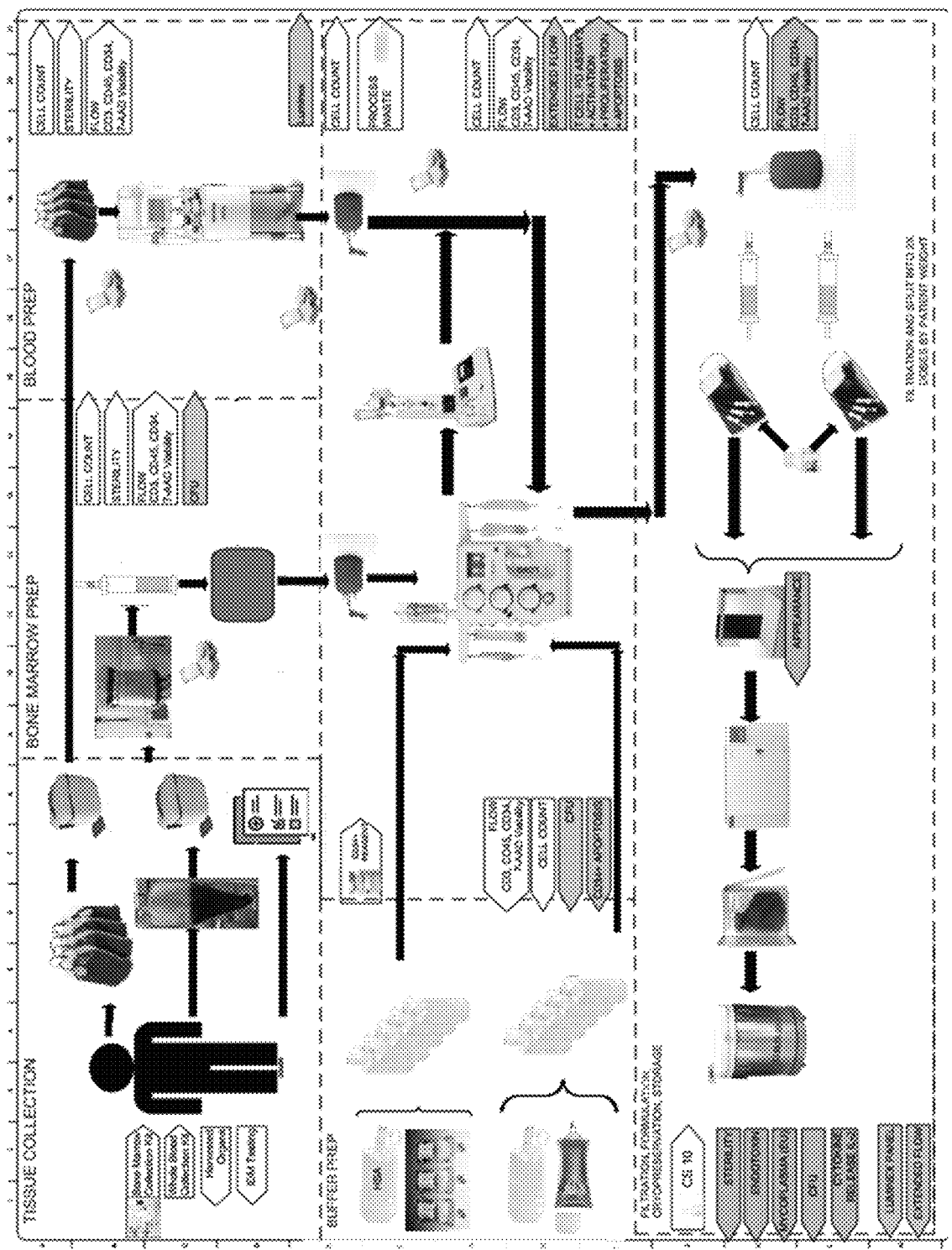
FIG. 5 is a flow diagram illustrating a method of preparing a cellular composition according to an embodiment of the invention.
Figure 6:
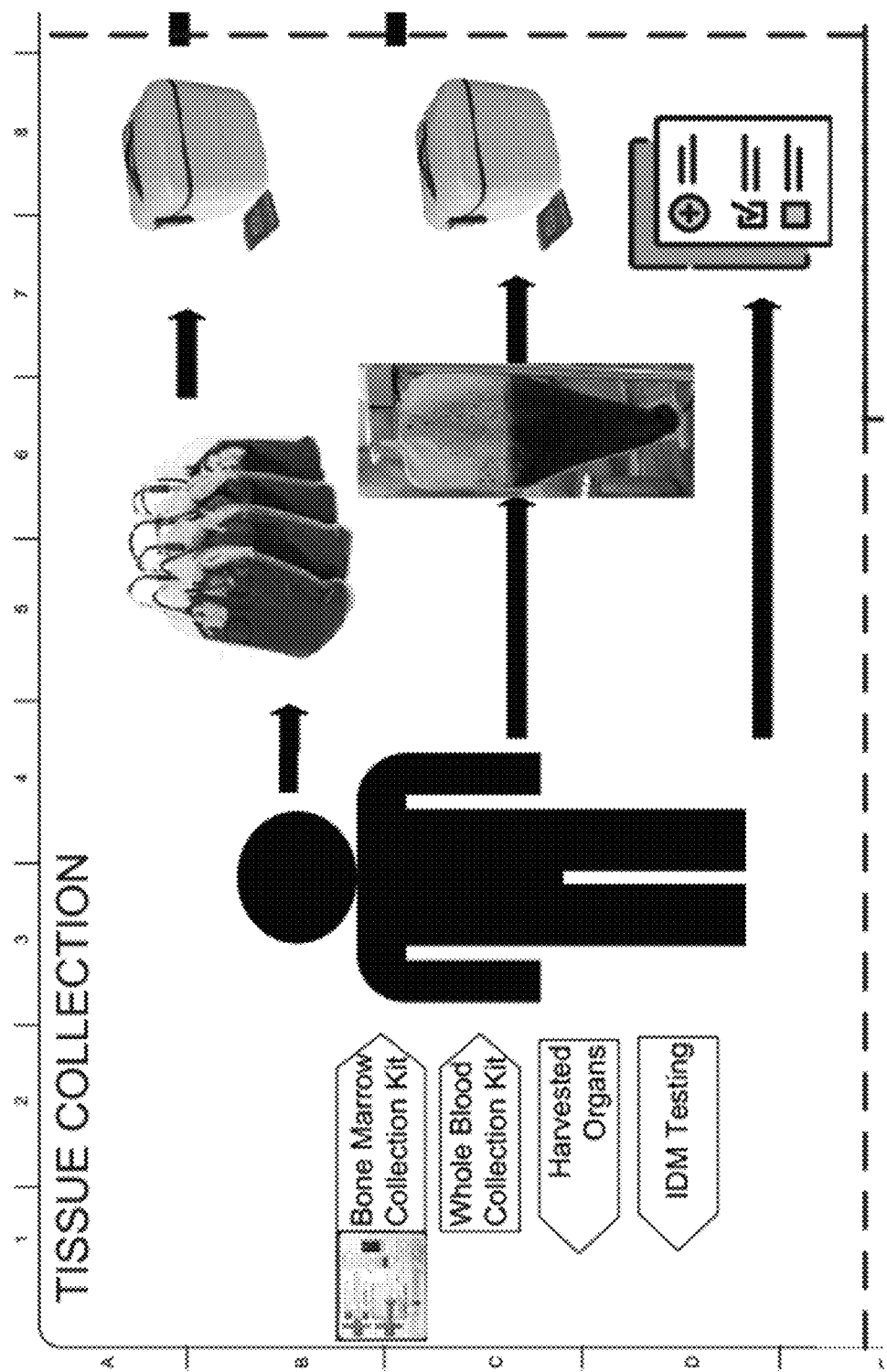
FIG. 6 is an expanded view of the tissue collection step from the flow diagram in FIG. 5.

FIG. 6 is an expanded view of the tissue collection step from the flow diagram in FIG. 5. Blood, bone marrow, and one or more solid organs of interest are harvested from the body of a deceased donor. Bone marrow is extracted by trephination, as described above. Blood is collected into one or more receptacles of devices of the invention, as described above. Blood or other material from the body is tested for infectious disease markers (IDMs).

Figure 7:
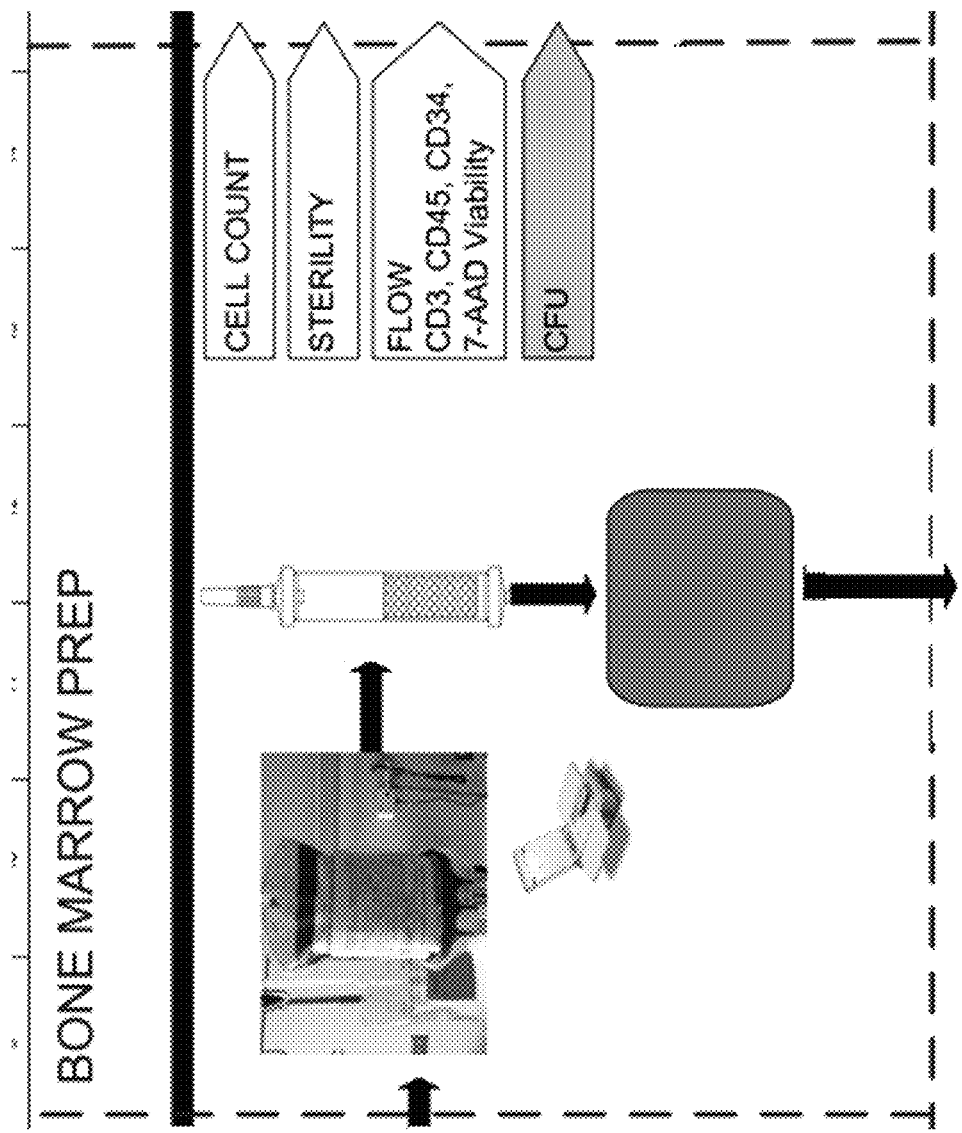
FIG. 7 is an expanded view of the bone marrow preparation step from the flow diagram in FIG. 5.

FIG. 7 is an expanded view of the bone marrow preparation step from the flow diagram in FIG. 5. The extracted bone marrow is passed through a sieve to remove bone shards, and it is depleted of red blood cells by one of the methods described above The bone marrow is also analyzed for cell number, sterility, viability, colony-forming ability, and expression of CD3, CD34, and CD45 markers. Viability is assayed by exclusion of 7-aminoactinomycin D (7-AAD), and marker expression is analyzed by flow cytometry.

Figure 8:
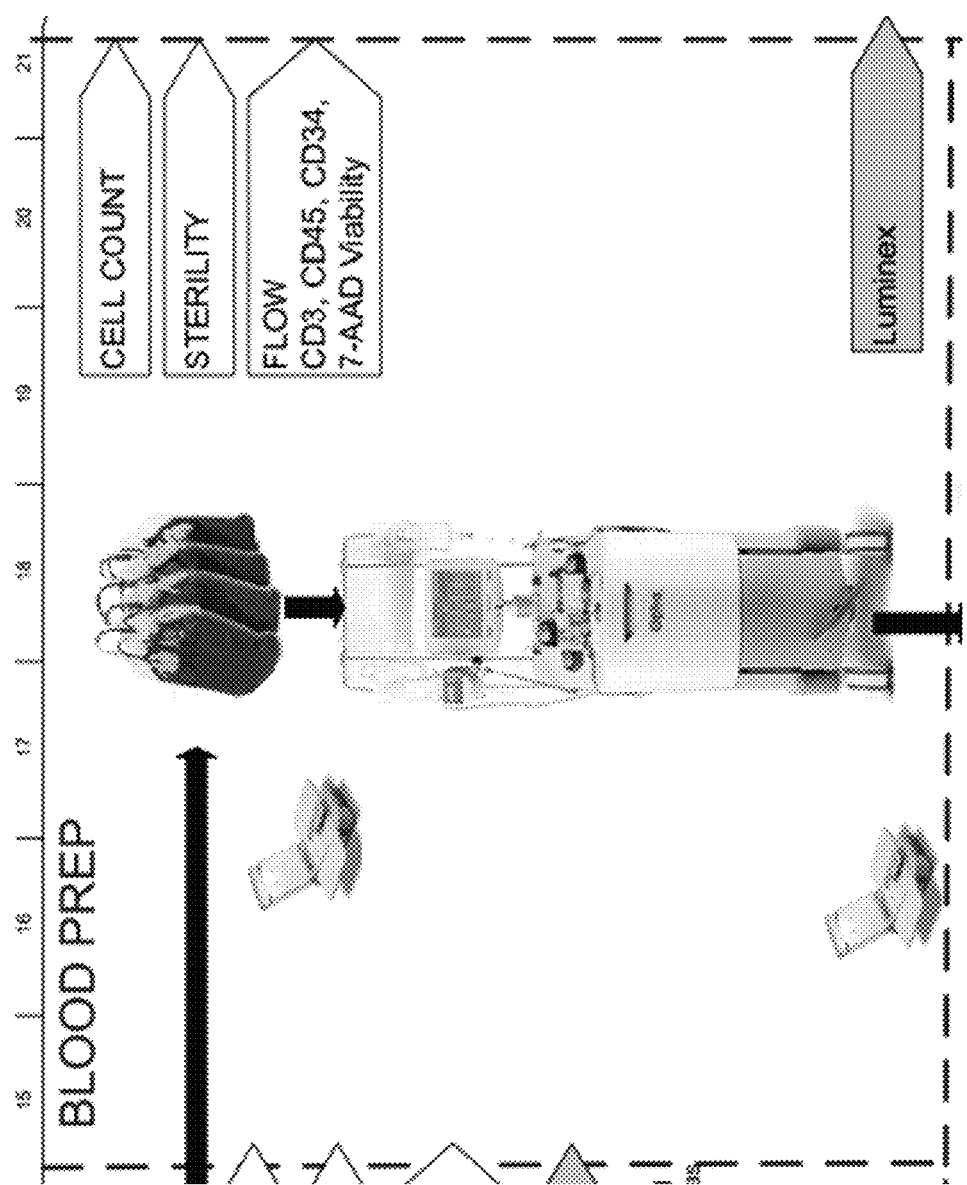
FIG. 8 is an expanded view of the step of the blood preparation step from the flow diagram in FIG. 5.

FIG. 8 is an expanded view of the step of the blood preparation step from the flow diagram in FIG. 5. The blood is depleted of red blood cells and platelets by one of the methods described above. The blood is also analyzed for cell number, sterility, viability, and expression of CD3, CD34, and CD45 markers. Viability is assayed by exclusion of 7-AAD, and marker expression is analyzed by flow cytometry.

Figure 9:
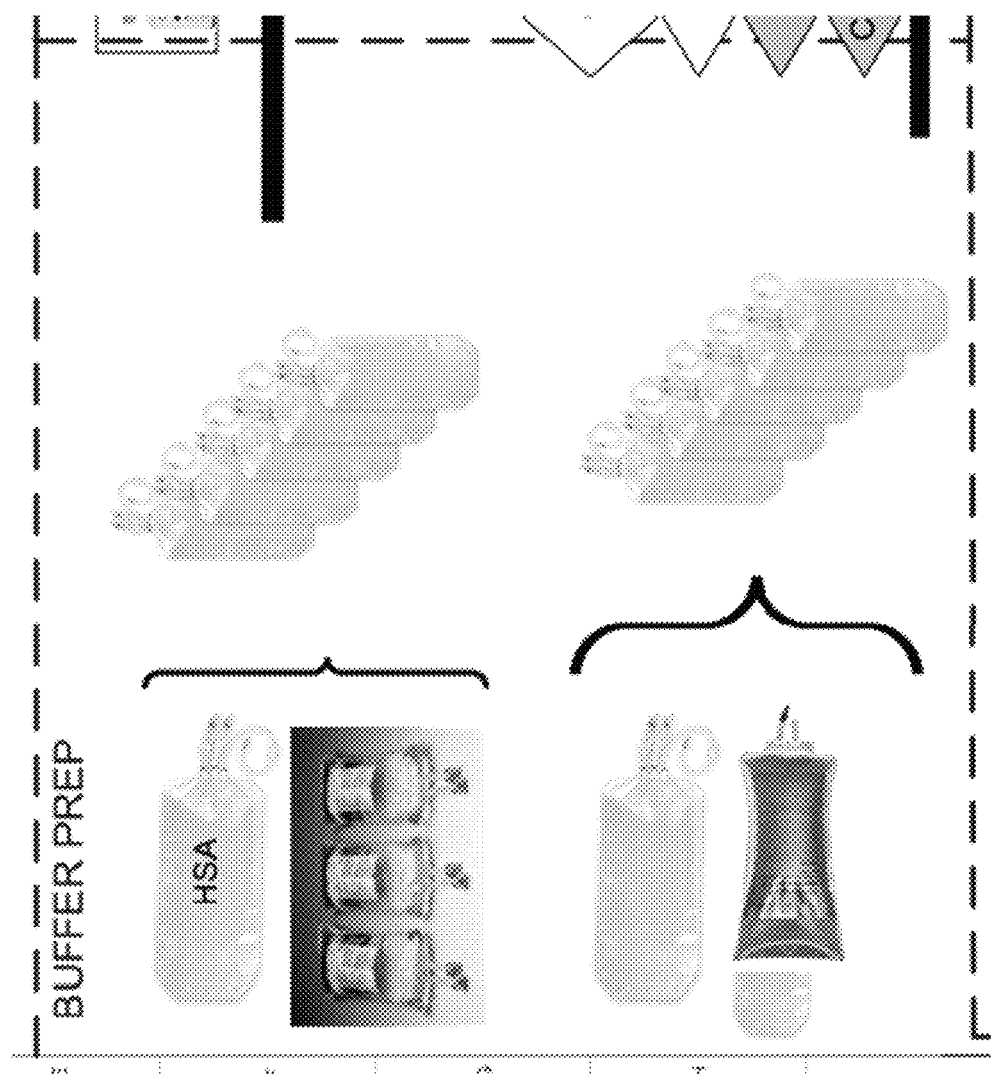
FIG. 9 is an expanded view of the buffer preparation step from the flow diagram in FIG. 5.

FIG. 9 is an expanded view of the buffer preparation step from the flow diagram in FIG. 5. Two buffers are prepared, one that contains HSA and another that contains a balanced electrolyte solution.

Figure 10:
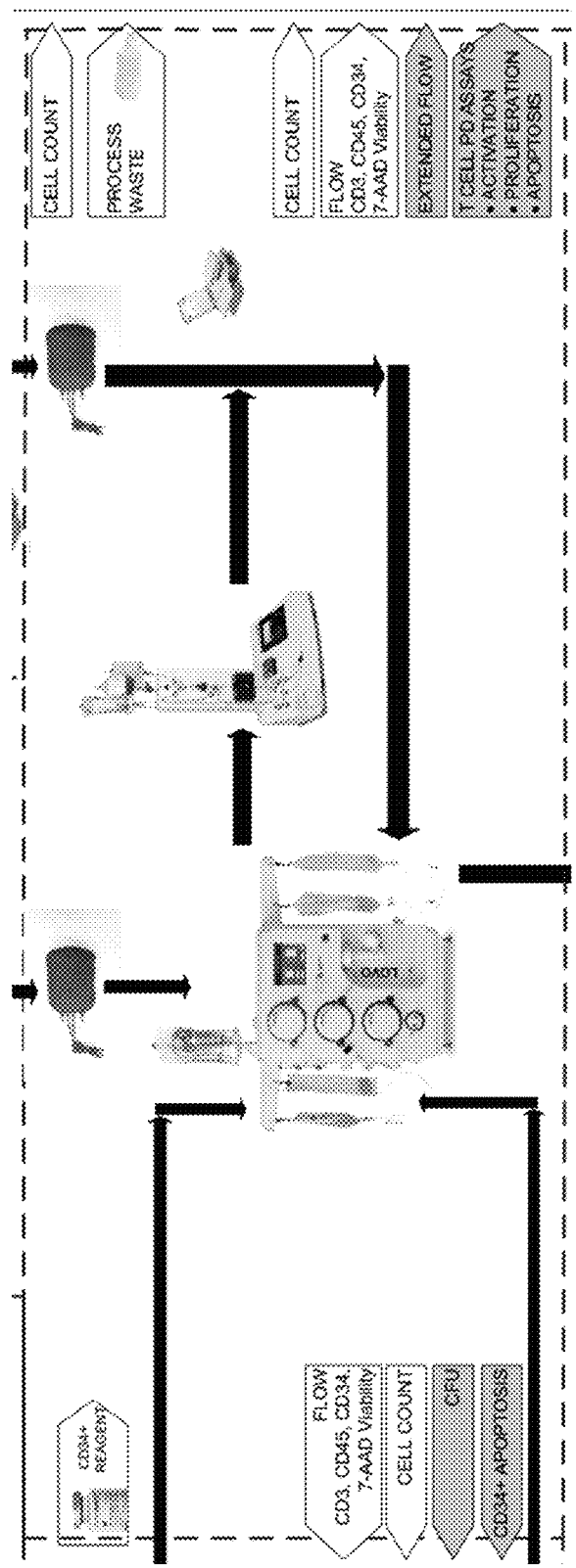
FIG. 10 is an expanded view of the $CD34^+$ cell-enrichment step from the flow diagram in FIG. 5.

FIG. 10 is an expanded view of the CD34$^+$ cell-enrichment step from the flow diagram in FIG. 5. The buffers are used with the cells obtained from the bone marrow preparation step to enrich for CD34$^+$ cells by spinning membrane filtration. The sample is further enriched for CD34$^+$ cells by immunomagnetic selection. Cell number, viability, colony-forming ability, and marker expression is analyzed as described above, either prior to or following spinning membrane filtration. Cells from the blood preparation step are analyzed for cell number, viability, marker expression, T cell activation, T cell proliferation, and T cell apoptosis, as described above. If the bone marrow-derived cells enriched for CD34$^+$ cells and the blood-derived cells containing CD3$^+$ cells are both determined to be suitable for use in a cellular product, the two cellular fractions are combined.

Figure 11:
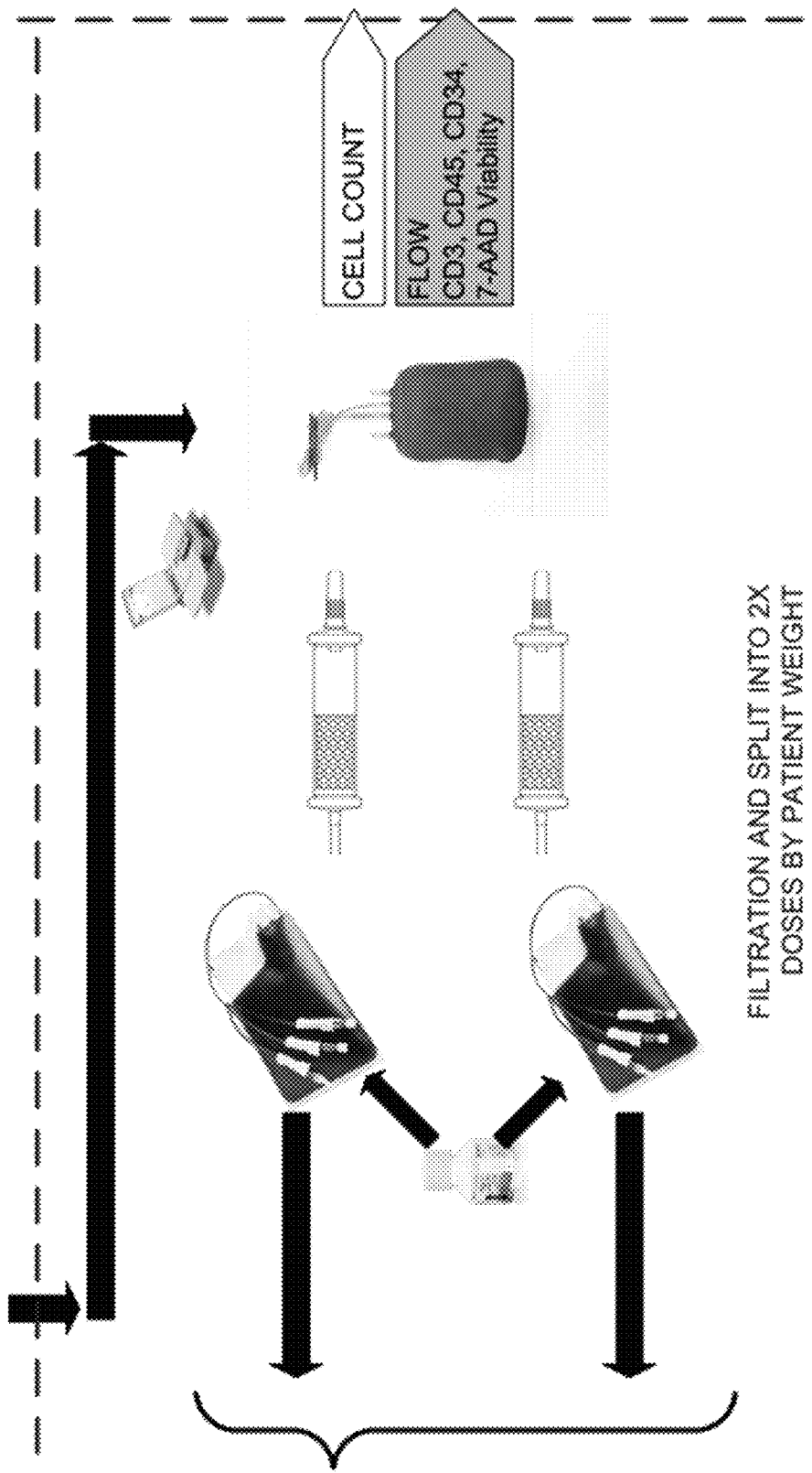
FIG. 11 is an expanded view of the dividing step from the flow diagram in FIG. 5.

FIG. 11 is an expanded view of the dividing step from the flow diagram in FIG. 5. Pooled cells are filtered to remove clots and cell clumps, i.e., agglutination. Pooled cells are then divided into two individual doses, each of which contains sufficient quantities of CD34$^+$ cells and CD3$^+$ cells to promote mixed chimerism in a separate organ transplant recipient. During this step, cell number, viability, and marker expression is analyzed, as described above. Cells may also be analyzed for sterility, endotoxins, mycoplasma, colony-forming ability, release of cytokines, e.g., IL-2.

Figure 12:
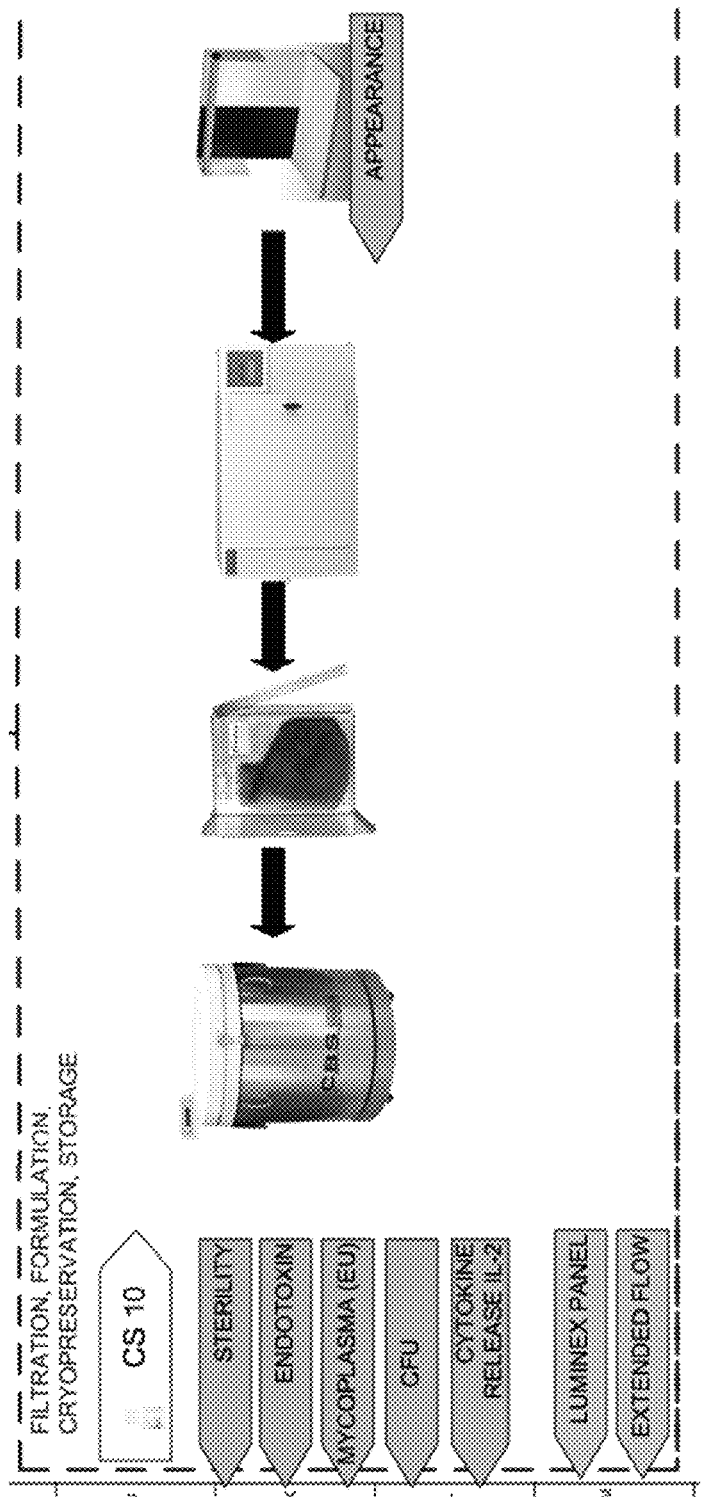
FIG. 12 is an expanded view of the cryopreservation step from the flow diagram in FIG. 5.

FIG. 12 is an expanded view of the cryopreservation step from the flow diagram in FIG. 5. Doses may be further divided into aliquots, or they may be maintained in a single container. Doses are frozen by in a freezer that reduces the temperature of the cellular products to a target temperature at a controlled rate. After the cellular products have reached the target temperature, they are transferred to liquid nitrogen for long-term storage.

Example 2

An exemplary process for preparing a cellular product, MDR-104, containing CD34$^+$ cells and CD3$^+$ cells is described below. The process provides two doses, each of which contains $100 \times 10^6$ T cells/kg recipient weight and $>4 \times 10^6$ CD34$^+$ cells/kg recipient weight, from a single deceased donor. Each dose supports transplantation of one kidney from the deceased donor into a different recipient. The product also includes >500 colony-forming units (CFUs) per $10^5$ cells. The product may be further characterized to determine IL-2 release and percentage of viable CD34$^+$ cells and CD3$^+$ cells.

Figure 13:
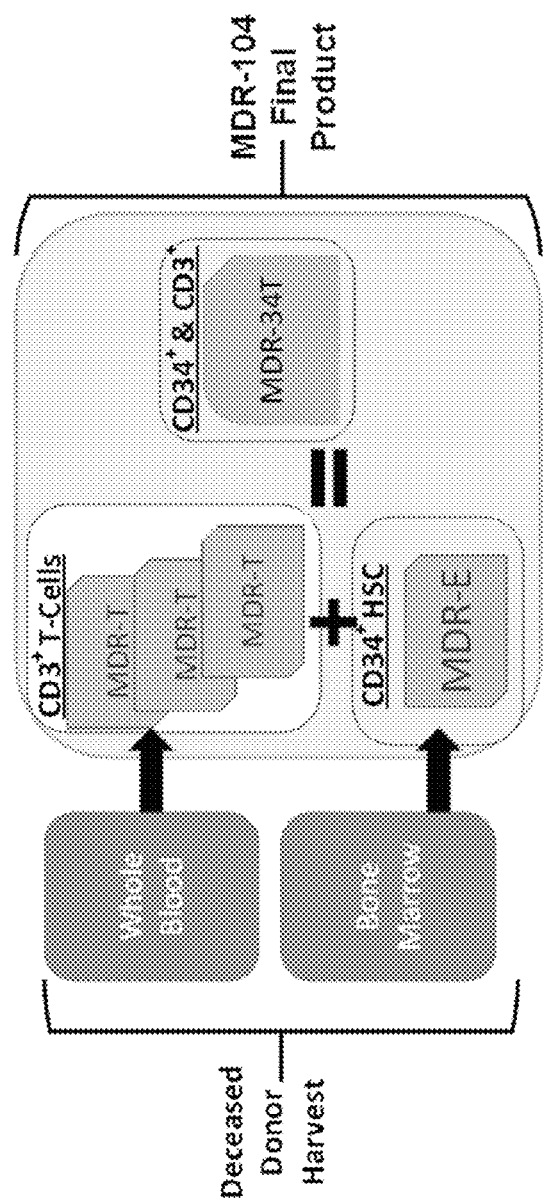
FIG. 13 is a flow diagram illustrating a method of preparing a cellular composition according to an embodiment of the invention.

FIG. 13 is a flow diagram illustrating a method of preparing a cellular composition according to an embodiment of the invention. As described in more detail below, CD3$^+$ cells are prepared from whole blood in MDR-T processing, CD34$^+$ are prepared from bone marrow in MDR-E processing, and the prepared CD3$^+$ cells and HSPCs are combined in MDR-34T processing.

Whole blood (WB) and bone marrow (BM) are collected as starting material to supply the requisite CD3$^+$ T cells and CD34$^+$ HSPCs, respectively, in the cellular compositions of the final drug product. The exsanguinated blood is collected following systemic heparinization of the deceased donor into either a single collection device or several smaller collection devices to permit ease of transport from the collection site to the manufacturing site. Whole blood is subsequently processed using an apheresis instrument for platelet and red blood cell depletion, then washed for additional platelet removal either prior to or following the addition of the CD34$^+$-selected, in-process intermediate.

Bone marrow is harvested via one or both of two methods. One method employs standard bone marrow aspiration from the exposed iliac crests of the deceased donor. In the second method, marrow is recovered via the trephine orthopedic device, which is capable of harvesting cores of cortical and cancellous bone containing BM. Bone marrow may also be recovered from deceased donor vertebral bodies. The bone marrow harvested by each of the two methods is placed in an appropriate shipping container to support transport of the recovered BM to the manufacturing site.

The isolated CD34$^+$ HSPCs are combined with the leukapherised blood product and separated as required to fulfill dose requirements for each recipient of the deceased donor kidneys. Each dose is formulated and cryopreserved as separate final drug product lots.

Whole blood collected from the deceased donor is utilized to supply the needed dose of CD3$^+$ T cells for each recipient of the deceased donor kidneys. CD34$^+$ HPSCs are isolated from harvested bone marrow to supply the needed dose of CD34$^+$ cells for each recipient of the donor kidney.

Whole blood is collected from the exsanguinated deceased donor. Exsanguination occurs following systemic heparinization and in conjunction with cold flush of preservative solution. The exsanguinated whole blood is egressed from the deceased donor via two cannulae from both arterial and venous supply and connected through sterile connections to a collection device for transport to the manufacturing site.

Deceased donor bone marrow is collected by one or both of two independent methods: standard bone marrow aspiration and marrow recovery via an orthopedic device, the trephine. Bone marrow aspiration is performed through repeated aspirations using a heparinized syringe and Jamshedie needle. The trephine device permits taking cores of bone marrow containing cancellous bone shards.

Exsanguinated blood is required to arrive at the manufacturing site with minimal hemagglutination, red cell lysis, and cell clumping, and with high leukocyte viability to facilitate downstream processing of red blood cell and platelet depletion. Whole blood is collected in devices that allow blood to be maintained at a controlled temperature and shipped in a stable sterile transport container. The collection devices are also compatible with closed system bioprocessing.

Bone marrow collected by either standard aspiration practices or trephination is required to arrive at the manufacturing site with minimal hemagglutination, red cell lysis, and cell clumping, and with high leukocyte viability to facilitate downstream processing of red blood cell, platelet depletion and $CD34^+$ HSPC isolation. Total $CD34^+$ yields and recoveries are tracked as an extrapolated metric. Total volume of harvested bone marrow is calculated for each method and extrapolated for each deceased donor.

Harvested bone marrow from the deceased donor undergoes downstream processing prior to being used as a starting material for $CD34^+$ HPSC isolation. Several methods and/or technologies may be employed to establish optimal methods to separate the hematopoietic marrow from cancellous bone shards and red blood cell depletion in order to obtain bone marrow mononuclear cells (BMMNCs).

The deceased donor blood is removed prior to harvesting the bone marrow.

Incoming bone marrow collected by needle aspiration is diluted with buffer and filtered with an appropriate filtration device to remove bone shards. One or more of the following methods may be used to obtain maximal recovery of mononuclear cells (MNCs): size-based centrifugal separation, hetastarch sedimentation, immunomagnetic depletion or lysis followed by a spinning membrane filtration wash step or buoyancy-activated cell separation.

Incoming bone marrow cores obtained using the trephine are processed by one more of physical agitation, enzymatic disaggregation, or washing and filtration to recover the hematopoietic marrow compartment embedded inside the cancellous cores.

Incoming bone marrow is analyzed for complete blood cell counts, sterility, and leukocyte viability via flow cytometric analysis using specific antigens on the cell surface of target cell populations including but not limited to CD45, CD34 and CD3. Data from flow cytometry analysis is used to determine $CD34^+$ viability, $CD34^+$ HSPC frequency, and quantification of $CD34^+$ cell counts as reference values from deceased donors.

The exsanguinated blood collected from the deceased donor is processed by apheresis into an appropriate starting material prior to formulation and cryopreservation.

The incoming whole blood receiving into the manufacturing facility processed to enrich for peripheral blood mononuclear cells to achieve an appropriate starting material for the MDR-104 manufacturing process. Incoming whole blood starting material first undergoes apheresis to reduce volume and obtain a comparable leukapheresis in-process material. Filtration of whole blood products is performed as necessary to remove clots and cell clumps from the incoming material as well as the resulting leukapheresis. The resulting leukapheresis in-process material is used to formulate the $CD3^+$ T cells dose for each recipient of the deceased donor's kidneys.

Incoming whole blood is analyzed for complete blood cell counts, sterility, and leukocyte viability via flow cytometric analysis using specific antigens on the cell surface of target cell populations including, but not limited to, CD45, CD34 and CD3. The potential to meet T cell dose expectations and T cell recoveries is calculated prior to and post apheresis.

The red blood cell-depleted, in-process material is utilized for the immunoselction of $CD34^+$ HSPCs. First, platelets are depleted, then the RBC- and platelet-reduced material undergoes CD34 immunoselection.

The red blood cell-depleted in-process material obtained from the bone marrow preparation sub-process is further depleted of platelets using spinning membrane filtration.

Next, the RBC- and platelet-reduced sample is incubated with a CD34-capture reagent, washed using spinning membrane filtration to remove unbound beads, and loaded onto the immunomagnetic column system for immunoselection of the $CD34^+$ HSPCs.

Incoming bone marrow is analyzed for complete blood cell counts, sterility, and leukocyte viability via flow cytometric analysis using specific antigens on the cell surface of target cell populations, including, but not limited to, CD45, CD34 and CD3. The potential to meet $CD34^+$ cell dose expectations and $CD34^+$ recoveries is calculated prior to and post immunoselection.

MDR-104 is a combined product dose formulation in which the $CD34^+$ HSPCs are combined with the required T cell number to fulfill the $CD3^+$ dose requirements. First, the MDR-E subprocess is divided into two separate bags in sufficient $CD34^+$ cell numbers to meet the minimum dose requirements of $>4\times10^6$ $CD34^+$ cells/kg for each deceased donor kidney recipient. $CD3^+$ T cells quantified in the whole blood preparation sub-process are then be added to each MDR-E preformulation bag to meet the required $CD3^+$ T cell dose of $100\times10^6$ CD3 T cells/kg.

MDR-T34 represents the sub-process step of combining the MDR-E derived from the $CD34^+$ immunoselection with the requisite T cell dose derived from the resulting leukapheresis of the whole blood preparation unit of operation.

The MDR-E process intermediate is quantified for viable $CD34^+$ HSPCs and then separated into pre-formulation bags based on the required patient dose of $>4\times10^6$ viable $CD34^+$ cells/kg. Viable CD3 T cells are quantified from the leukapheresis process intermediate, and $100\times10^6$ cells/kg of viable CD3 T cells are added to each of the MDR-E preformulation bags based on the T cell dose requirements for each respective patient. Each pre-formulated intermediate then undergoes an additional spinning membrane filtration step to further reduce the platelet concentration.

Platelet burden and efficiency to platelet reduction are monitored pre and post spinning membrane filtration. $CD34^+$ HSPC and $CD3^+$ T cell lose are also monitored pre and post spinning membrane filtration. Complete cell counts and quantitative flow cytometry are used to monitor frequencies and viability of target cell populations. Functional assays are employed as necessary to ensure that sufficient T cells and $CD34^+$ HSPCs with expected functional characteristics are maintained at dose requirements.

The resulting pre-formulated process intermediates are combined at a ratio of 1:2 with CryoStor 10 (CS10) to generate the drug substance and dispensed into 3-4 final drug product containers just prior to cryopreservation. The pre-formulated MDR-E and T cells are combined with cryoprotectant to generate the final product.

The preformulated MDR-T34 process intermediates for each recipient are combined with an equal volume of CS10 in the collection containers. Next, each product is divided across final product containers each at 50 mL total volume. The need for filtration is evaluated as needed prior to container closure and cryopreservation. Following the completion and container closure for both MDR-104 products, the final drug products undergo controlled cryopreservation using control rate freezers and transferred to vapor phase liquid $N_2$ for long-term storage at $\leq-150°$ C.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A cellular product for establishing mixed chimerism in a solid organ transplant recipient, the product comprising:
   greater than $1 \times 10^5$ CD34$^+$ cells/kg recipient weight derived from bone marrow obtained from a deceased donor, wherein said obtained bone marrow is contacted with an agent that mobilizes CD34+ cells; and
   greater than $1 \times 10^5$ CD3$^+$ cells/kg recipient weight derived from non-bone marrow of the deceased donor.

2. The cellular product of claim 1, wherein the bone marrow is derived from iliac crests or vertebral bodies.

3. The cellular product of claim 1, wherein the non-bone marrow is selected from the group consisting of blood, liver, lymph nodes, spleen, and thymus.

4. The cellular product of claim 3, wherein the non-bone marrow is blood.

5. The cellular product of claim 1, wherein the CD34$^+$ cells and the CD3$^+$ cells are HLA-matched to the solid organ transplant recipient.

6. The cellular product of claim 1, wherein the CD34$^+$ cells and the CD3$^+$ cells are HLA-mismatched to the solid organ transplant recipient.

7. The cellular product of claim 1, wherein the CD34$^+$ cells and the CD3$^+$ cells are provided in separate containers.

8. The cellular product of claim 1, wherein the CD34$^+$ cells and the CD3$^+$ cells are provided as a mixture in a common container.

9. The cellular product of claim 1, further comprising a cryopreservation medium.

10. The cellular product of claim 9, wherein the cryopreservation medium comprises at least one cryoprotectant selected from the group consisting of DMSO and dextran having a molecular weight of about 40,000 Da.

11. The cellular product of claim 1, wherein the mobilizing agent is granulocyte colony stimulating factor (G-CSF).

* * * * *